United States Patent
Smith et al.

(10) Patent No.: US 7,367,939 B2
(45) Date of Patent: May 6, 2008

(54) ROTATIONAL, TRANSLATIONAL AND TORQUEING CONTROL MEMBERS FOR AN ENDOSCOPIC INSTRUMENT

(75) Inventors: Kevin W. Smith, Coral Gables, FL (US); Jose Luis Francese, Miami Springs, FL (US); Juergen A. Kortenbach, Miami Springs, FL (US); Robert Sixto, Jr., Miami, FL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 327 days.

(21) Appl. No.: 10/867,395

(22) Filed: Jun. 14, 2004

(65) Prior Publication Data

US 2005/0277951 A1 Dec. 15, 2005

(51) Int. Cl.
*A61B 1/00* (2006.01)
(52) U.S. Cl. .............. 600/104; 600/139; 600/142; 600/143; 600/144; 600/145; 600/151
(58) Field of Classification Search ............. 606/139, 606/142–145, 151
See application file for complete search history.

(56) References Cited

U.S. PATENT DOCUMENTS

| 4,038,987 A | | 8/1977 | Komiya .................... 128/321 |
| 4,741,336 A | | 5/1988 | Failla et al. ............... 128/334 |
| 5,049,133 A | * | 9/1991 | Villen Pascual ............ 604/110 |
| 5,156,609 A | * | 10/1992 | Nakao et al. ............... 606/142 |
| 5,170,800 A | | 12/1992 | Smith et al. |
| 5,222,961 A | | 6/1993 | Nakao et al. |
| 5,383,880 A | * | 1/1995 | Hooven ..................... 606/142 |
| 5,403,326 A | | 4/1995 | Harrison et al. ............ 606/139 |
| 5,433,721 A | | 7/1995 | Hooven et al. ............. 606/143 |
| 5,439,156 A | | 8/1995 | Grant et al. .............. 227/179.1 |
| 5,460,168 A | * | 10/1995 | Masubuchi et al. ......... 600/123 |
| 5,484,451 A | * | 1/1996 | Akopov et al. ............ 606/139 |
| 5,497,933 A | | 3/1996 | DeFonzo et al. ......... 227/175.1 |
| 5,499,998 A | | 3/1996 | Meade |
| 5,562,694 A | | 10/1996 | Sauer et al. ................ 606/176 |

(Continued)

OTHER PUBLICATIONS

"What Endoscopic Accessories Do We Really Need?", C. Paul Swain, Emerging Technologies in Gastrointestinal Encoscopy, *Gastrointest. Endosc.*, vol. 7, No. 2, pp. 313-330 (Apr. 1997).

*Primary Examiner*—Linda C. M. Dvorak
*Assistant Examiner*—Matthew J. Kasztejna
(74) *Attorney, Agent, or Firm*—Gordon & Jacobson, PC

(57) ABSTRACT

A flexible endoscopic clip applier includes a flexible coil with a manual actuator coupled to one end and a jaw assembly coupled to the other end. A store of clips is arranged adjacent to the jaw assembly and a clip pusher is arranged adjacent to the store of clips. The actuator includes a lever for opening and closing the jaws, a knob for rotating the jaw assembly, and a crank for dispensing clips. The knob and the lever are coupled to a single control member which extends through the coil to a joiner where it is joined to a pair of pull wires coupled to the jaws. The crank is coupled to a second control member which is threaded along a distal portion. The threaded portion engages a threaded member near the pusher and is coupled to the pusher such that rotation of the threaded control member by the crank causes the pusher to be moved distally.

3 Claims, 46 Drawing Sheets

U.S. PATENT DOCUMENTS

| | | | |
|---|---|---|---|
| 5,582,617 A | 12/1996 | Kleiman | 606/170 |
| 5,601,224 A | 2/1997 | Bishop et al. | |
| 5,601,573 A | 2/1997 | Fogelberg et al. | 606/143 |
| 5,667,517 A | 9/1997 | Hooven | 606/151 |
| 5,707,392 A | 1/1998 | Kortenbach | |
| 5,725,537 A | 3/1998 | Green et al. | |
| 5,769,857 A * | 6/1998 | Reztzov et al. | 606/143 |
| 5,792,165 A | 8/1998 | Klieman et al. | 606/170 |
| 5,797,536 A | 8/1998 | Smith et al. | |
| 5,833,695 A | 11/1998 | Yoon | 606/139 |
| 5,849,019 A | 12/1998 | Yoon et al. | |
| 5,865,724 A | 2/1999 | Palmer et al. | |
| 5,904,693 A | 5/1999 | Dicesare et al. | |
| 5,921,993 A | 7/1999 | Yoon | |
| 5,941,439 A | 8/1999 | Kammerer et al. | 227/67 |
| 5,993,465 A | 11/1999 | Shipp et al. | 606/142 |
| 6,193,651 B1 | 2/2001 | DeFonzo | |
| 6,269,819 B1 * | 8/2001 | Oz et al. | 128/898 |
| 6,331,165 B1 | 12/2001 | Turturro et al. | |
| 6,350,269 B1 | 2/2002 | Shipp et al. | |
| 6,352,503 B1 * | 3/2002 | Matsui et al. | 600/104 |
| 6,423,079 B1 | 7/2002 | Blake, III | |
| 6,530,933 B1 | 3/2003 | Yeung et al. | |
| 6,533,157 B1 | 3/2003 | Whitman | |
| 6,544,271 B1 | 4/2003 | Adams et al. | |
| 6,824,548 B2 | 11/2004 | Smith et al. | |
| 6,905,057 B2 | 6/2005 | Swayze et al. | |
| 6,926,676 B2 | 8/2005 | Turturro et al. | |
| 7,223,272 B2 | 5/2007 | Francese et al. | |
| 2002/0138086 A1 | 9/2002 | Sixto et al. | |
| 2002/0198539 A1 | 12/2002 | Sixto et al. | |
| 2002/0198541 A1* | 12/2002 | Smith et al. | 606/142 |
| 2003/0191478 A1 | 10/2003 | Kortenbach et al. | |
| 2004/0193185 A1 | 9/2004 | McBrayer | |
| 2005/0049616 A1 | 3/2005 | Rivera et al. | |
| 2005/0090837 A1 | 4/2005 | Sixto, Jr. et al. | |
| 2005/0277952 A1 | 12/2005 | Arp et al. | |
| 2005/0277954 A1 | 12/2005 | Smith et al. | |
| 2005/0277955 A1 | 12/2005 | Palmer et al. | |
| 2005/0277956 A1 | 12/2005 | Francese et al. | |

* cited by examiner

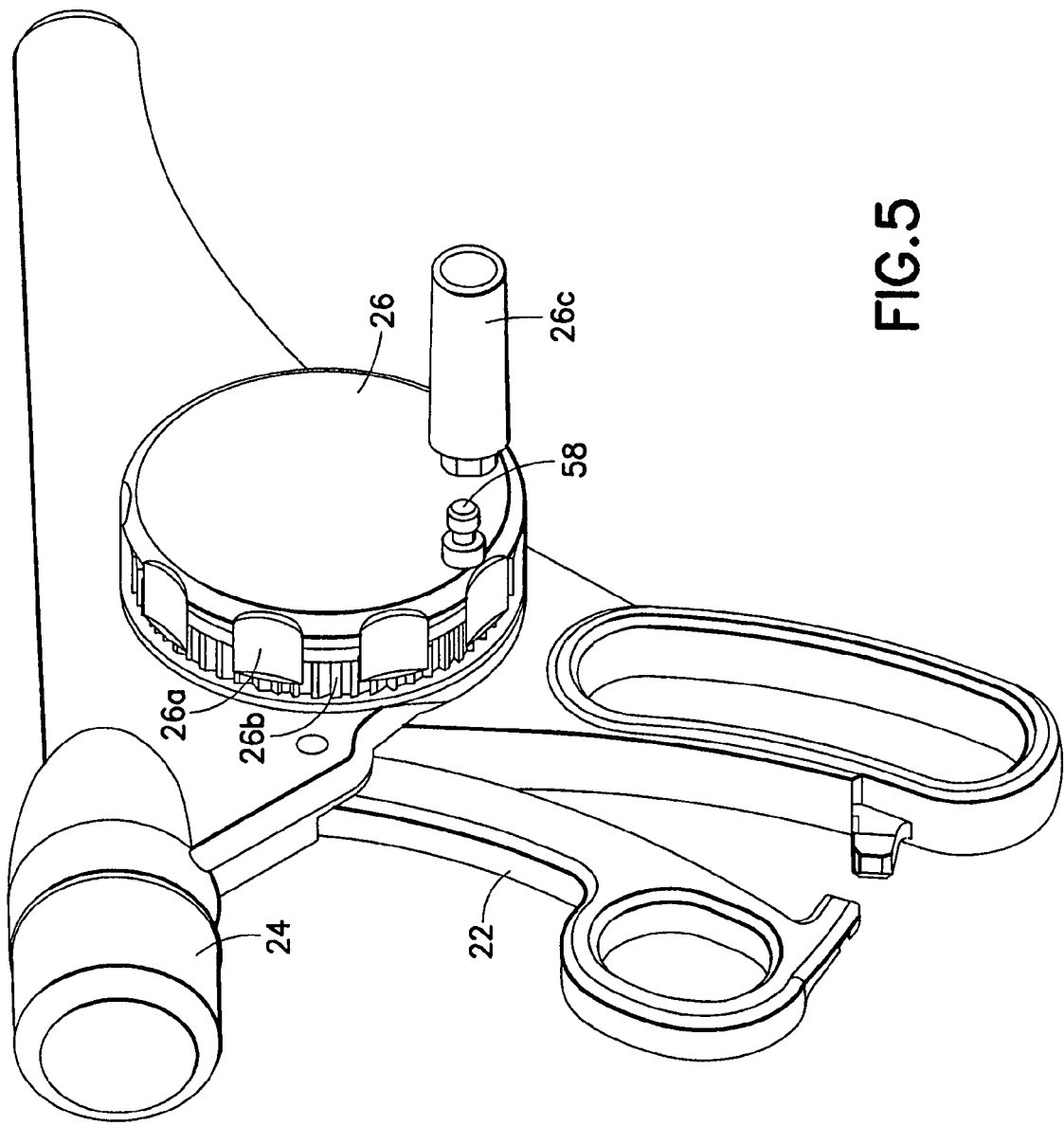

ROTATIONAL, TRANSLATIONAL AND TORQUEING CONTROL MEMBERS FOR AN ENDOSCOPIC INSTRUMENT

This application is related to U.S. Ser. No. 10/867,412 entitled "SURGICAL CLIP", filed on an even date herewith, the complete disclosure of which is hereby incorporated by reference herein.

BACKGROUND OF THE INVENTION

1. Field of the Invention

This invention relates broadly to surgical instruments. Particularly, this invention relates to flexible endoscopic instruments for use through an endoscope. More particularly, this invention relates to a surgical clip applier which is adapted for use through an endoscope and may be used to clamp and/or suture, ducts, vessels, and other tissues, to anchor a tissue, or to attach a foreign body to a tissue.

2. State of the Art

Surgical clips are generally used to apply clamping force to ducts, vessels, and other tissues. In addition, surgical clips are particularly useful in controlling bleeding of a tissue in lieu of suturing or stapling where suturing or stapling is difficult.

Surgical clips are typically applied to tissue by clip appliers. All of the currently available surgical multi-firing clip appliers are substantially rigid devices intended to extend through a trocar port or through an incision to a surgical site requiring application of a clip. The devices have been rigid because a stiff pushing element has been required in order to exert the required pushing force to move the clip over the tissue.

There is a substantial need for a flexible clip applier, particularly one insertable through a lumen of an endoscope. The ability to apply clips through an endoscope would permit myriad minimally invasive surgical solutions to medical problems, especially those of the gastrointestinal tract. However, it is accepted theory that the transmitted force required to advance or form a clip over tissue cannot be produced in the distal end of a long flexible device that is commonly constructed with a metal tubular coil, or polymer tube, such as an endoscopic device or catheter.

Generally a flexible endoscopic device (e.g., a biopsy forceps device) includes an outer tubular member, typically being constructed of a metal tubular coil or a polymer tube which is poor in transmitting forces that impart tensile stresses to the outer tubular member, a control element longitudinally movable relative to the tubular member, an end effector coupled to the distal ends of both the tubular member and the control element such that relative movement of the control element and the tubular member causes operation of the end effector, and a handle which moves the control element relative to the handle. This type of flexible endoscopic instrument is limited in the amount of pushing force it can generate for several reasons. First, compression of a flexible control element (pushing element) tends to cause the pushing element to buckle within the outer flexible sheath of the device. If a relatively larger diameter flexible pushing element is used such that it better resists buckling, the pushing element may impart too much stiffness to permit it to flex as it bends with the endoscopic instrument. Second, a flexible pushing element of larger diameter is subject to greater frictional forces within the outer sheath, which reduces the force transmitted from the handle to the end effector. If the flexible pushing element is made relatively smaller in diameter, it is subject to kinking, which will result in little to no force being transmitted to the distal end. Kinking is especially a problem in endoscopic instruments, because the endoscope and its lumen may be extended through a tortuous path. For most flexible devices, especially metal coils, the outer sheath begins to stretch when force is applied to the pushing element. This reduces or eliminates the force and relative movement of the pushing element. For these reasons and others, mechanical application of a relatively large distal end pushing force, and particularly clip application, have been absent from the capability of flexible endoscopic tools.

In addition, it is important that the tissue about which a clip is to be applied be substantially compressed. While the jaws apply a clamping force which compresses the tissue, large clamping forces are difficult to achieve because of the dimensions of the relatively small jaw assembly. That is, the dimensions are such that the lever arm between a pivot of the jaw assembly and each jaw tang is relatively short, limiting the mechanical leverage of the jaw assembly.

Our previous application Ser. No. 10/396,962, which is hereby incorporated by reference herein in its entirety, discloses a flexible clip applier that includes a ratchet mechanism adapted to locate a clip pusher to a known location after deployment of a clip. In addition, the clip applier includes a flexible housing into which a train of clips may be chambered. The flexible housing does not elongate when subject to tensile forces. In addition, the jaw assembly is adapted to have relatively high mechanical leverage which facilitates tissue compression prior to application of a clip.

Since the development of the clip applier disclosed in Ser. No. 10/396,962, we have developed an improved flexible endoscopic clip applier which is the subject of the instant application.

SUMMARY OF THE INVENTION

It is therefore an object of the invention to provide a flexible endoscopic clip applier.

It is also an object of the invention to provide a flexible endoscopic clip applier capable of dispensing multiple clips.

It is another object of the invention to provide a flexible endoscopic clip applier which limits the amount of force which can be applied to the jaws of the device.

It is still another object of the invention to provide a flexible endoscopic clip applier which limits the amount of force which can be applied to the jaws of the device while adjusting for relative changes in the length of the outer sheath due to tortuosity of the path of the endoscope.

It is a further object of the invention to provide a flexible endoscopic clip applier which has two jaws which are rotatable about different axes to improve the mechanical advantage of the jaws.

It is also an object of the invention to provide a flexible endoscopic clip applier which dispenses clips via smooth movement of a manual actuator.

It is an additional object of the invention to provide a flexible endoscopic clip applier which has an actuator that dispenses clips precisely one at a time.

Another object of the invention is to provide a flexible endoscopic clip applier which uses a single control wire to open and close jaws as well as to rotate them about the longitudinal axis.

A further object of the invention is to provide a flexible endoscopic clip applier having improved jaws.

An additional object of the invention is to provide a flexible endoscopic clip applier which prevents the accidental dispensing of the penultimate clip when the device is moved away from the ultimate clip after it is applied.

It is yet another object of the invention to provide a flexible endoscopic clip applier which forms clips as they are dispensed.

It is even another object of the invention to provide a flexible endoscopic clip applier having a handle having a resistance force which is substantially constant during a cycle of forming and applying a clip.

Yet another object of the invention is to provide a clip applier with clip-forming jaws which indicate a tissue fixation point for the applied clip.

Even another object of the invention is to provide a clip applier with a mechanism which stably advances clips through a coil and into an end effector.

A further object of the invention is to provide an endoscopic clip applier which can fire a clip only when the jaws of the applier are closed.

Another object of the invention is to provide an endoscopic clip applier which can fire only one clip at a time, i.e. between closing and opening the jaws.

An additional object of the invention is to provide an endoscopic clip applier which provides a visual indication to the practitioner of the number of clips which are left in the applier.

Still another object of the invention is to provide an endoscopic clip applier which stops operating after all of the clips have been dispensed.

In accord with these objects, which will be discussed in detail below, a flexible endoscopic clip applier according to the invention has a relatively long flexible coil (or tube) having a proximal end and a distal end. As used herein, the term proximal end means the end closest to the practitioner and the term distal means the end closest to the patient. A manual actuator is coupled to the proximal end of the coil and a pair of jaws is coupled to the distal end of the coil. A store of clips is disposed inside the coil adjacent to the jaws. The interiors of the jaws form anvils for bending a clip as it is pushed from the store into the closed jaws. The manual actuator has three controls: a lever for opening and closing the jaws, a knob for rotating the jaws (and a distal portion of the coil) about the longitudinal axis of the coil, and a crank for dispensing a clip. The lever and knob are coupled to a single first control member which extends through the coil to a point proximal of the store of clips. The crank is coupled to a second control member which extends through the coil up to a point adjacent to the store of clips and is threaded along a distal portion thereof.

According to the presently preferred embodiment, the lever is coupled to a force limiter which prevents too much force from being applied to the jaws when closing them. The force limiter also effectively adjusts for the relative changes in the length of the outer sheath with respect to the jaw control member. The knob is coupled to the first control member via a spline coupling. The crank is coupled to the second control member via a transmission and an energy storage device, e.g. a flywheel.

The first control member terminates proximal of the store of clips and is coupled to a joiner which is coupled to a pair of pull wires. The pull wires extend on opposite sides of the store of clips, each being coupled to one of the jaws.

According to the invention, the coil is bifurcated proximal of the store of clips and the two portions of the coil are joined by a rigid member having four bores, one of which is threaded. The rigid member is disposed distal of the joiner and the first control member extends into one of the bores of the rigid member. In this way, rotation of the first control member causes the rigid member to rotate which causes the distal portion of the coil and the jaws to rotate about the longitudinal axis. This helps orient the jaws properly before closing the jaws on a tissue to be clipped. The two pull wires extend through two other bores in the rigid member and the threaded portion of the second control member threadably engages the threaded bore of the rigid member. In this way, when the threaded control member is rotated (by the crank), it is translated distally. The distal end of the threaded control member is coupled to a clip pusher. The clip pusher is arranged adjacent to the proximally closest clip in the store of clips which are axially arranged one after the other. When the threaded control member is translated distally, the store of clips is moved distally until the ultimate clip (the one at the distal end of the store) enters the closed jaws and is applied to tissue through the bending of its ends by the interior anvils of the jaws.

The transmission and the pitch of the threads on the threaded portion of the second control member are arranged such that exactly one rotation of the crank causes exactly one clip to be dispensed. The crank is preferably provided with a detent lock which must be engaged to release the crank and which automatically stops the crank after one rotation.

Further according to the invention, the jaws are identical hermaphroditic jaws which are respectively rotatably coupled on offset axes to a clevis at the distal end of the distal coil. Each jaw has a distal tooth and a proximal tang. The tang is coupled to one of the pull wires and lies on one side of the longitudinal axis. The distal tooth of that jaw lies on the opposite side of the longitudinal axis, which prevents side-to-side misalignment of the jaws when they are closed.

The store of clips is housed in a "garage" which is coupled to the clevis and extends proximally therefrom. The garage is a substantially rigid rectilinear structure which keeps the clips properly aligned and allows them to be smoothly pushed out of the garage into the closed jaws. The distal portion of the garage is provided with a pair of biased stops which prevent the penultimate clip from moving out of the garage when the applier is moved away from the ultimate clip after it has been applied. In an alternate embodiment, the stops are made part of the clevis rather than the garage.

According to presently preferred embodiments, the crank is located on both sides of the manual actuator to accommodate left hand and right hand use. A counter mechanism is coupled to the crank and indicates the number of clips remaining in the garage. The detent lock is engagable by the lever so that the crank can only be operated when the jaws are closed. The crank is also provided with a ratchet mechanism so that it can only be rotated in one direction. The counter also includes a stop which prevents the crank from being rotated after all of the clips have been dispensed.

Additional objects and advantages of the invention will become apparent to those skilled in the art upon reference to the detailed description taken in conjunction with the provided figures.

BRIEF DESCRIPTION OF THE DRAWINGS

FIG. 5 is a perspective view of the manual actuator showing the crank;

FIG. 28b is an end view of the clip of FIG. 28a;

DETAILED DESCRIPTION OF THE PREFERRED EMBODIMENTS

Figure 1:
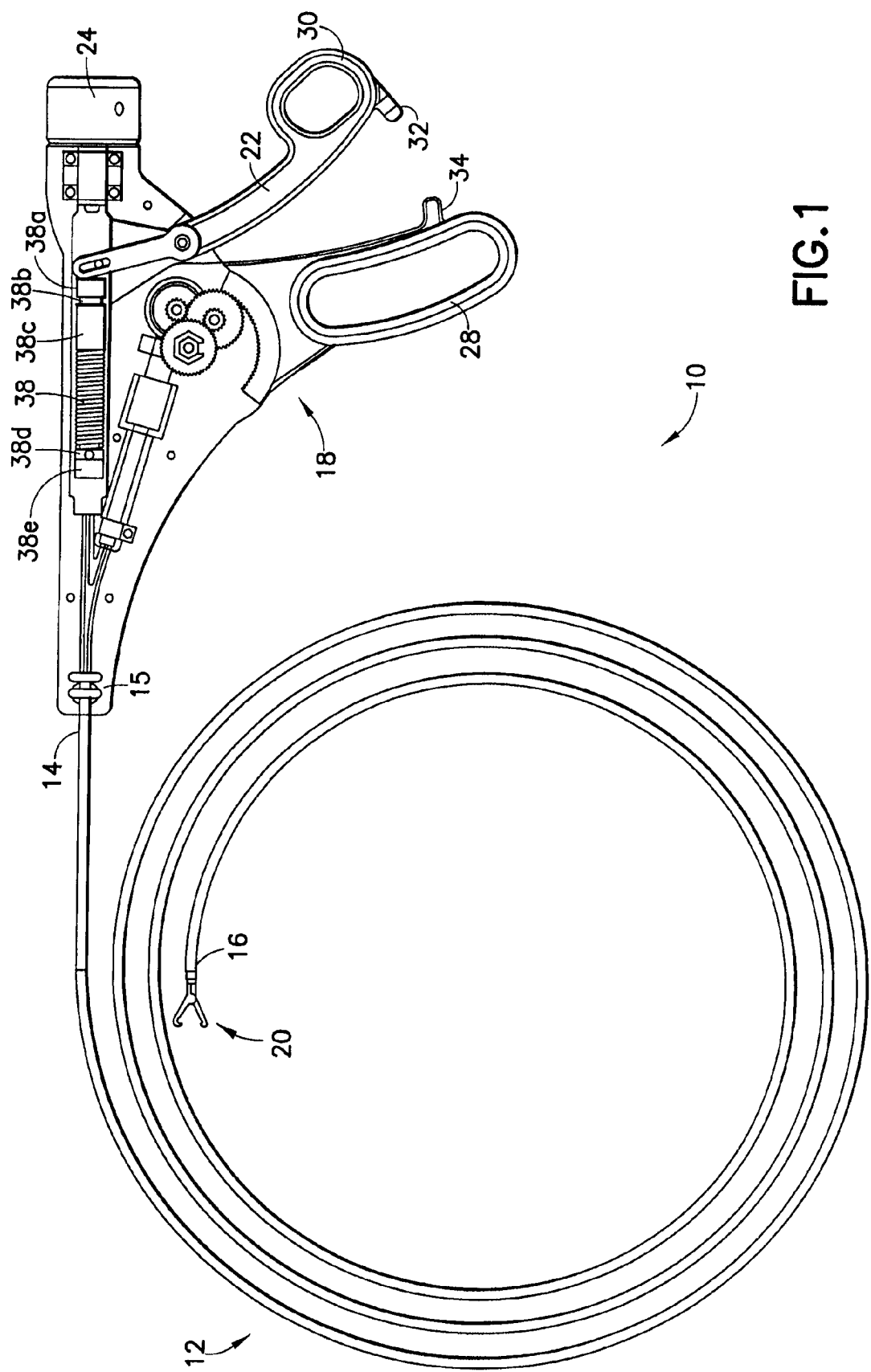
FIG. 1 is a partially disassembled side elevation view of a surgical clip applier according to the invention, shown with the lever and the jaws in an open position.

Turning now to FIG. 1, a flexible endoscopic clip applier 10 according to the invention has a relatively long flexible coil (or tube) 12 having a proximal end 14 and a distal end 16. As used herein, the term "proximal" means closest to the practitioner and the term "distal" means closest to the patient. A manual actuator 18 is coupled to the proximal end 14 of the coil 12 and a pair of jaws 20 is coupled to the distal end 16 of the coil 12. The coil is preferably a flat wire coil having a friction reducing outer sheath (not shown). The invention will be described in detail referring to each of its major components starting at the proximal end and working toward the distal end.

The Manual Actuator

A first embodiment of a manual actuator is shown in FIGS. 1-6. A presently preferred embodiment of the manual actuator is shown in FIGS. 30-37 and described in detail below.

Figure 4:
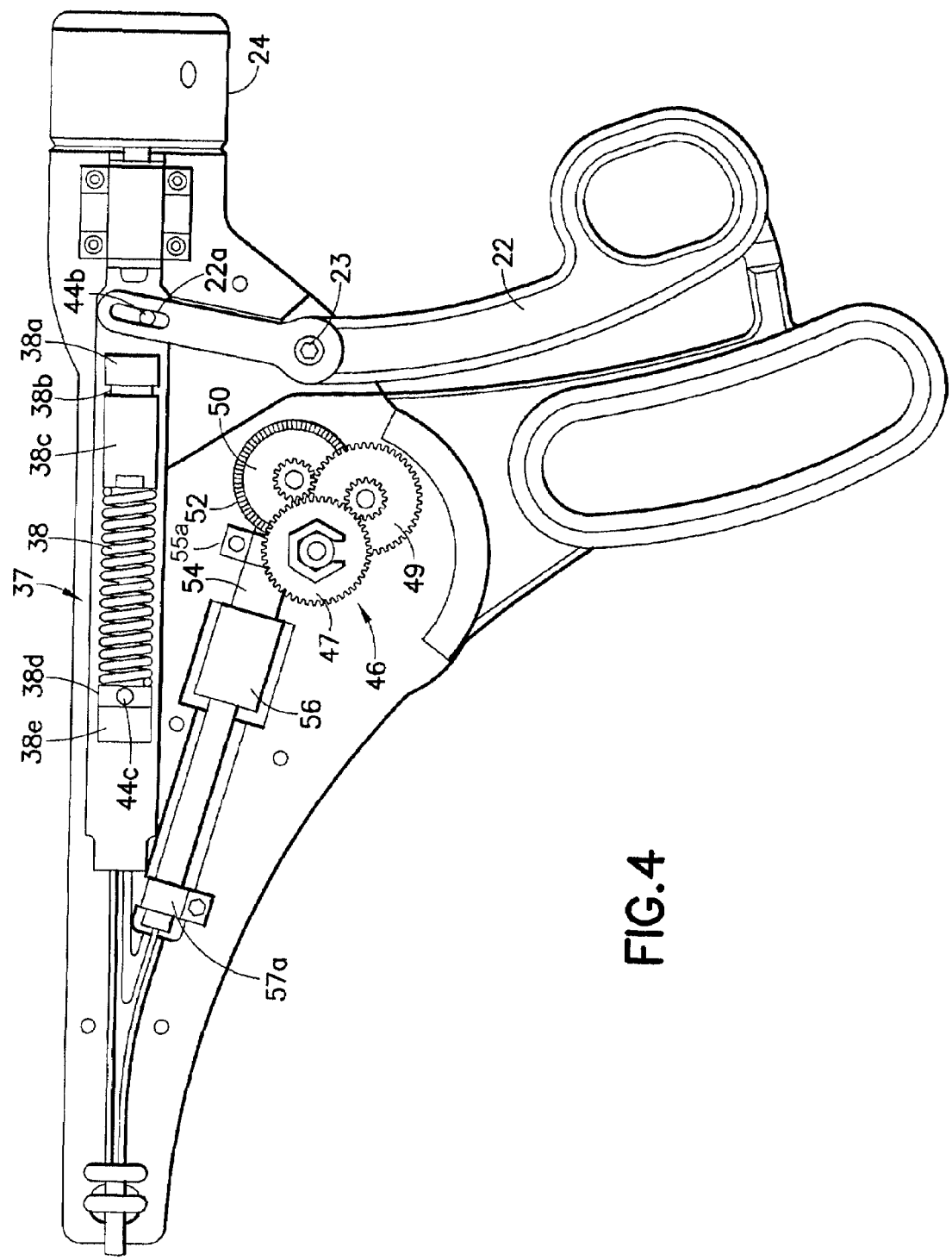
FIG. 4 is a longitudinal sectional view of the manual actuator shown with the lever in the closed position.

The manual actuator 18 of FIGS. 1-6 has three controls: a lever 22 for opening and closing the jaws 20, a knob 24 for rotating the jaws 20 (and a distal portion of the coil 12) about the longitudinal axis of the coil, and a crank 26 for dispensing a clip. It will be appreciated that the manual actuator 18 has a generally pistol shape which is similar to other endoscopic actuators. A finger grip 28 is provided opposite the lever 22 which has a thumb grip 30. Engaging hooks 32, 34 on the lever and the finger grip allow the lever to be locked as shown in FIG. 4. Those skilled in the art will further appreciate that the general operation of the clip applier 10 involves closing the jaws (optionally by locking the lever 22), delivering the jaws 20 through the lumen of an endoscope to the surgical site, opening the jaws as shown in FIG. 1, positioning the jaws 20 through movement of the coil 12 and rotation of the knob 24 so that tissue to be clipped is located between the jaws, locking the lever 22 to close the jaws on the tissue, turning the crank 26 to apply a clip, and then releasing the jaws from the clip and tissue.

Turning now to the details of the manual actuator 18 and with continued reference to FIGS. 1-6, and FIG. 3 in particular, the lever 22 and the knob 24 are coupled to a single first control member 36. The lever 22 is rotatable about axle 23 and coupled to the control member 36 via a force limiting mechanism 37. The force limiting mechanism includes spring 38, a proximal coupler 38a, a force limiter cap 38b, a force limiting cup 38c, an overload nut 38d, a distal coupler 38e, and an overload shaft 38f. The overload shaft 38f is coupled to overload nut 38d and extends inside the spring 38 and partially into the force limiting cup 38c.

Figure 2:
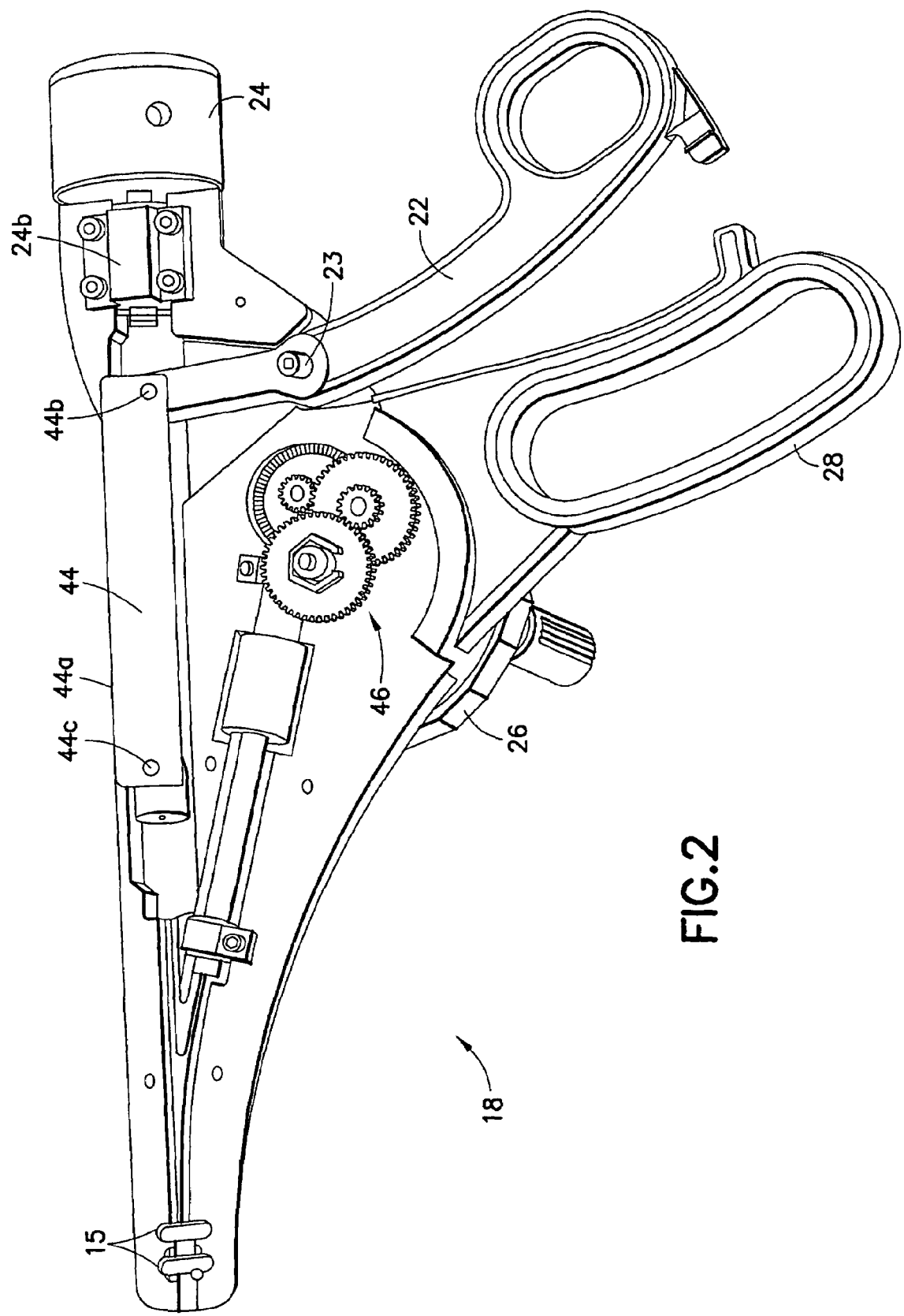
FIG. 2 is a partially disassembled perspective view of the manual actuator shown with the lever in the open position.

The lever 22 is coupled to the distal end of the spring 38 by a linkage 44 seen best in FIG. 2. In particular, the linkage 44 includes a U-shaped member 44a which fits over the spring 38 and its associated elements 38a-38f. A pin 44b couples the proximal end of the U-shaped member 44a to a slot 22a in the upper part of the lever 22 and a second pin 44c couples the distal end of the U-shaped member 44a to the overload nut 38d.

With the provided arrangement, movement of the lever 22 towards the finger grip 28 causes the linkage 44 to move proximally which moves the overload nut 38d proximally. The overload nut 38d in turn pushes against the spring 38 moving it proximally. The spring 38 pushes against the cup 38c which presses against the limiter cap 38b which in turn presses against the proximal coupling 38a. Since the proximal coupling 38a is affixed to the control member 36, proximal movement of the proximal coupling 38a causes proximal movement of the control member 36. Effectively, then, the entire force limiting assembly 37 is moving proximally and pulls the control member 36 proximally.

Figure 3:
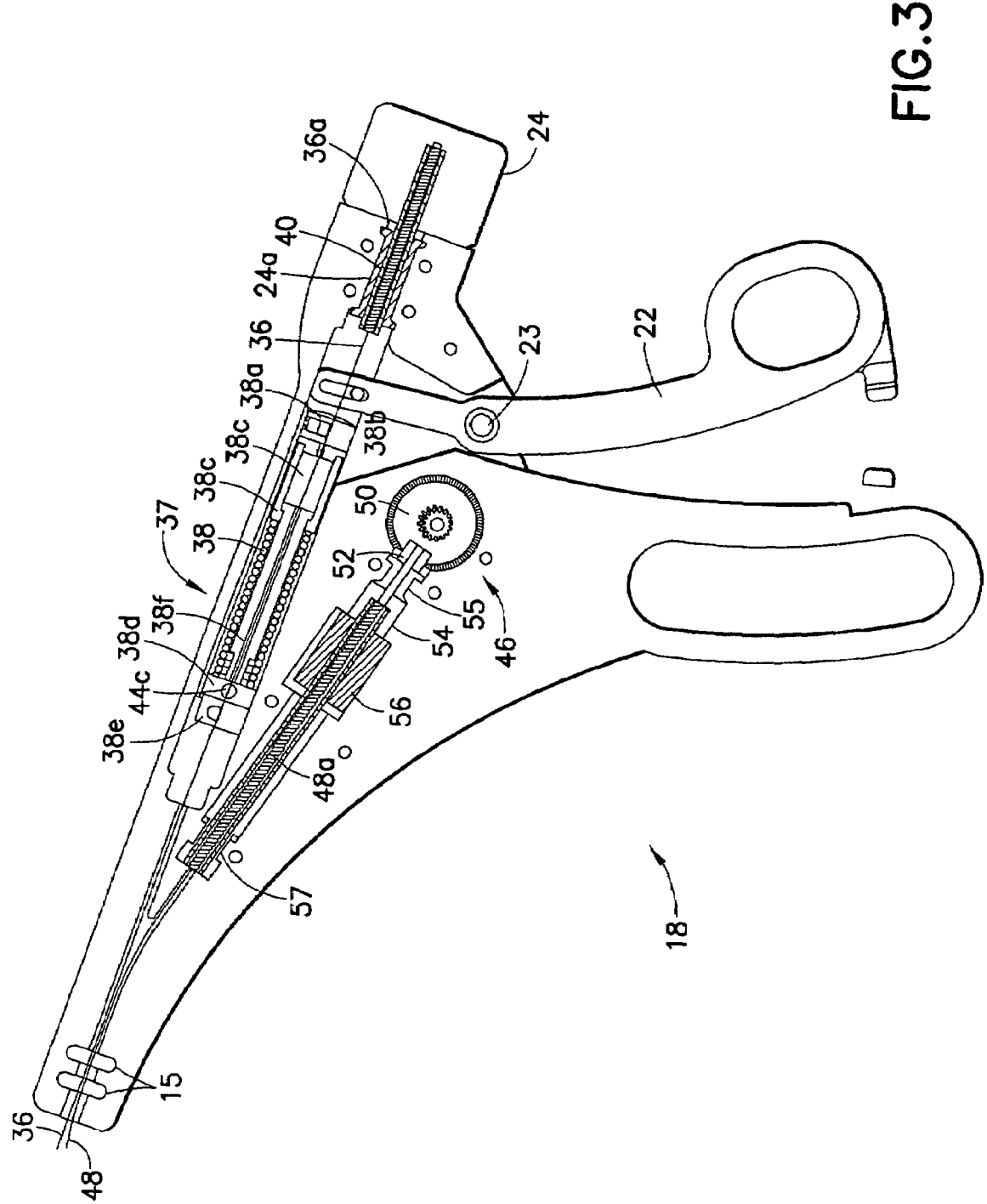
FIG. 3 is a longitudinal sectional view of the manual actuator shown with the lever in the open position.
Figure 3A:
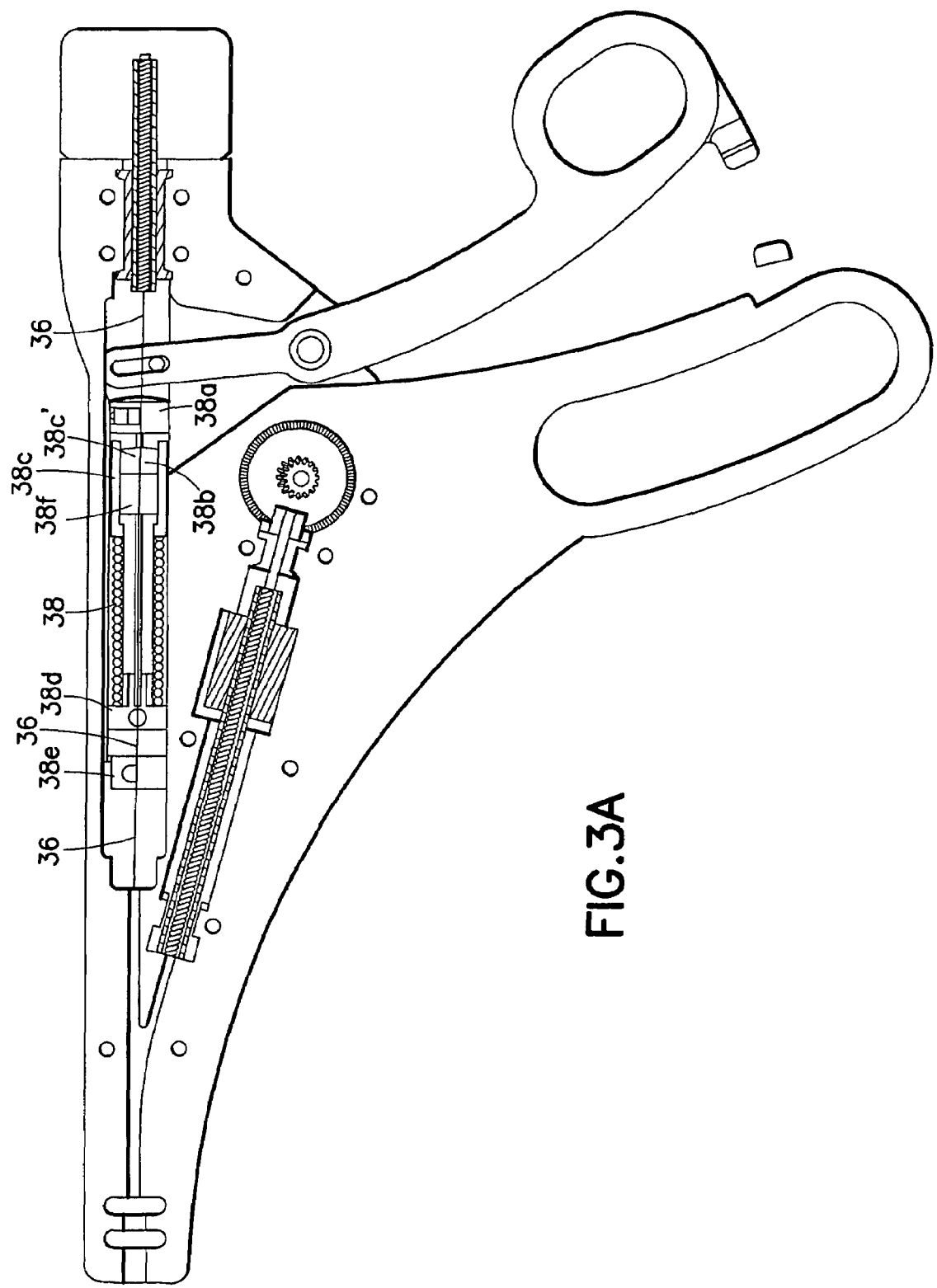
FIG. 3A is a view similar to FIG. 3 but showing the force absorbing spring in a compressed state.

If at any time during the closing of the jaws the tension on the control member 36 exceeds a predetermined force limit of the spring 38 (e.g., seventeen pounds), the spring force of the spring 38 will be overcome such that the spring 38 will compress and the overload shaft 38f and the overload nut 38d will move away from the distal coupler 38e without moving the control member 36 as seen in FIG. 3A. In this force overload situation, the shaft 38f is received into the hollow 38c' of the force limiting cup 38c.

FIG. 3A shows the force limiting spring 38 in the compressed position during closing of the jaws. This will occur when the control member 36 is pulled beyond the distance normally necessary to close the jaws (e.g. when the jaws are prevented from closing all the way because they are surrounding a very thick or very hard tissue, or if the tortuosity of the path of the coil causes an effective lengthening of the coil, effective shortening of the control member 36, thereby increasing the stroke of the lever 22, shortening the stroke required to close the jaws). The spring 38 prevents the jaws, the tissue and/or the control member 36 from being damaged due to excessive loads while allowing the lever 22 to be fully actuated to the latched position.

Figure 4A:
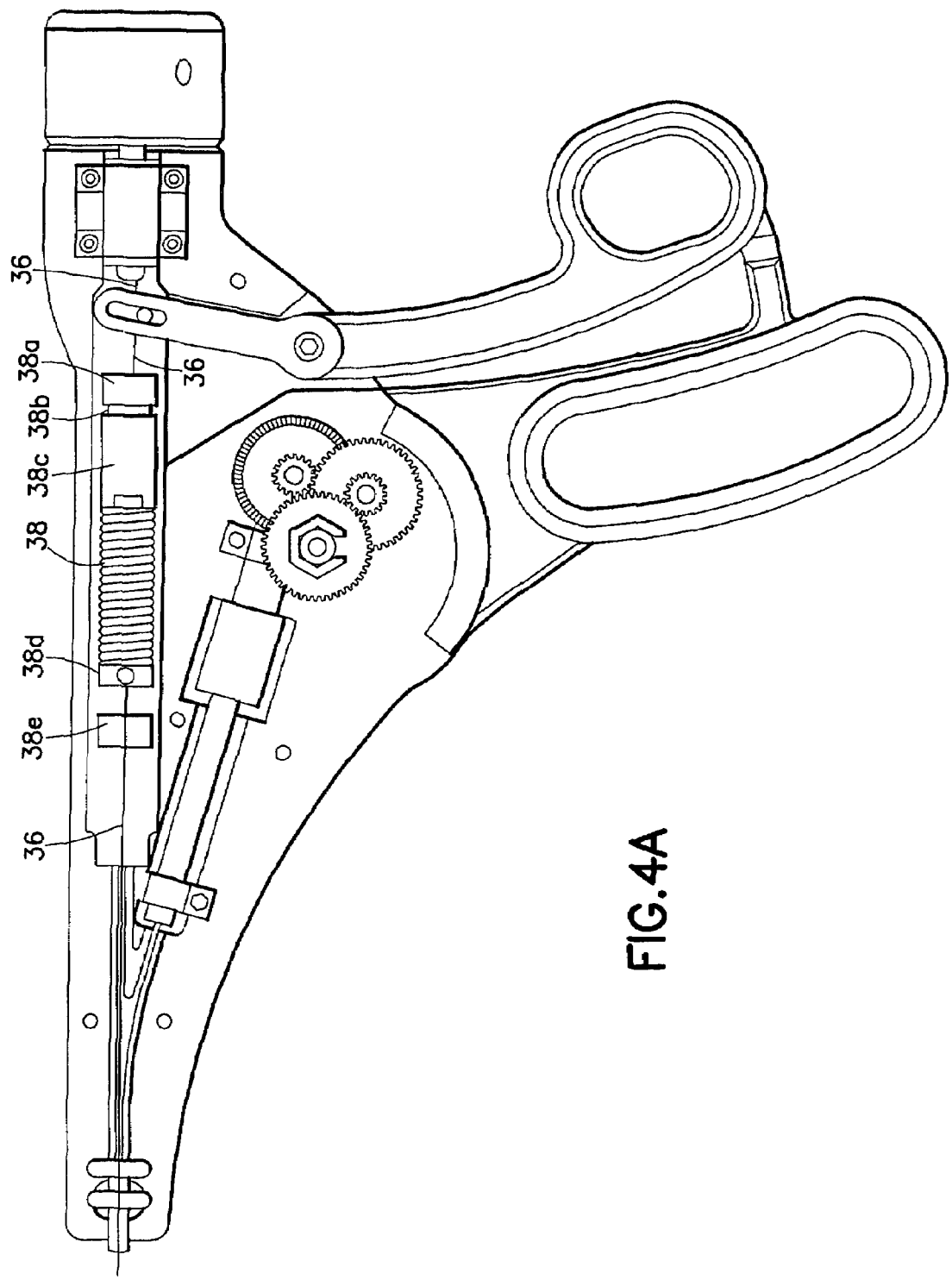
FIG. 4A is a view similar to FIG. 4 showing the force absorbing spring in a compressed state.

If, after the lever 22 has moved to a position as shown in FIG. 4 where the jaws have been closed, excessive force is applied to the control member 36 (e.g., while delivering the jaws to the surgical site through a tortuous endoscopic path), the force limiting mechanisms 37 will also operate to prevent damage to the control member 36. In particular, as seen in FIG. 4A, if the control wire is pulled distally after the jaws have been closed, and the force on the control wire 36 exceeds the predetermined limit of spring 38, the proximal coupling 38a which is fixedly coupled to the control member 36 will be moved distally against the cap 38b and the force limiting cup 38c. The force limiting cup, in turn will move distally, compressing the spring 38 against the nut 38d which is fixed in place because of its linkage to lever 22 which is locked.

In either case, when the lever 22 is released, the spring 38 will decompress by linkage 44 causing the nut 38d to move distally until it abuts the distal coupling 38e (which is coupled to the control member 36). The distal movement of the nut 38d causes distal movement of the distal coupling 38e which is coupled to the control member 36 causing the control member 36 to move distally.

According to the presently preferred embodiment, the spring is always compressed when the lever 22 is moved to the locked position.

Figure 29:
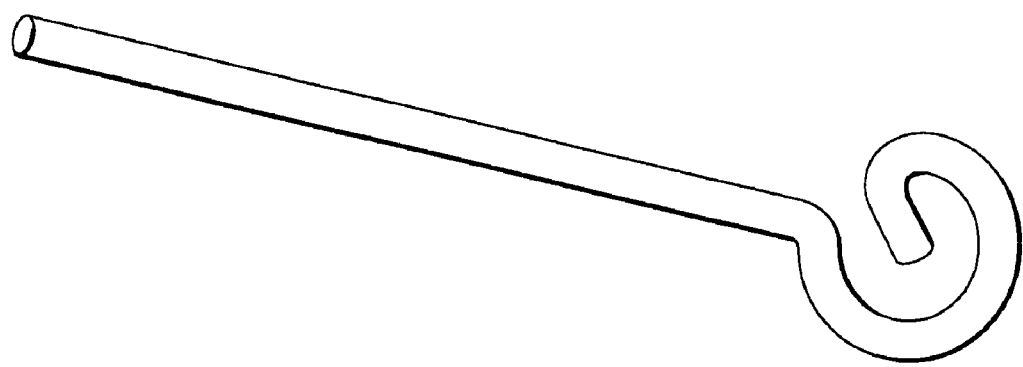
FIG. 29 is a perspective view of a shepard's crook.

To permit rotation of the control member 36, the knob 24 is coupled to the control member 36 via a spline 40 mounted in a shaft bearing 24a held by a clamp 24b. The proximal end of the control member 36 is bent into a shepherd's crook 36a which slidably engages the spline 40 coupled to the knob 24. A shepherd's crook is illustrated in FIG. 29. Rotation of the knob 24 thus causes rotation of the control member 36.

It should be noted that in the force limiting mechanism 37, the distal coupling 38e and the proximal coupling 38a are assembled in such a way as to allow clearance with the rest of the force limiting assembly 37. This clearance allows for ease of rotation since friction created by the preloaded spring 38 is not translated into torsional resistance.

Figure 4B:
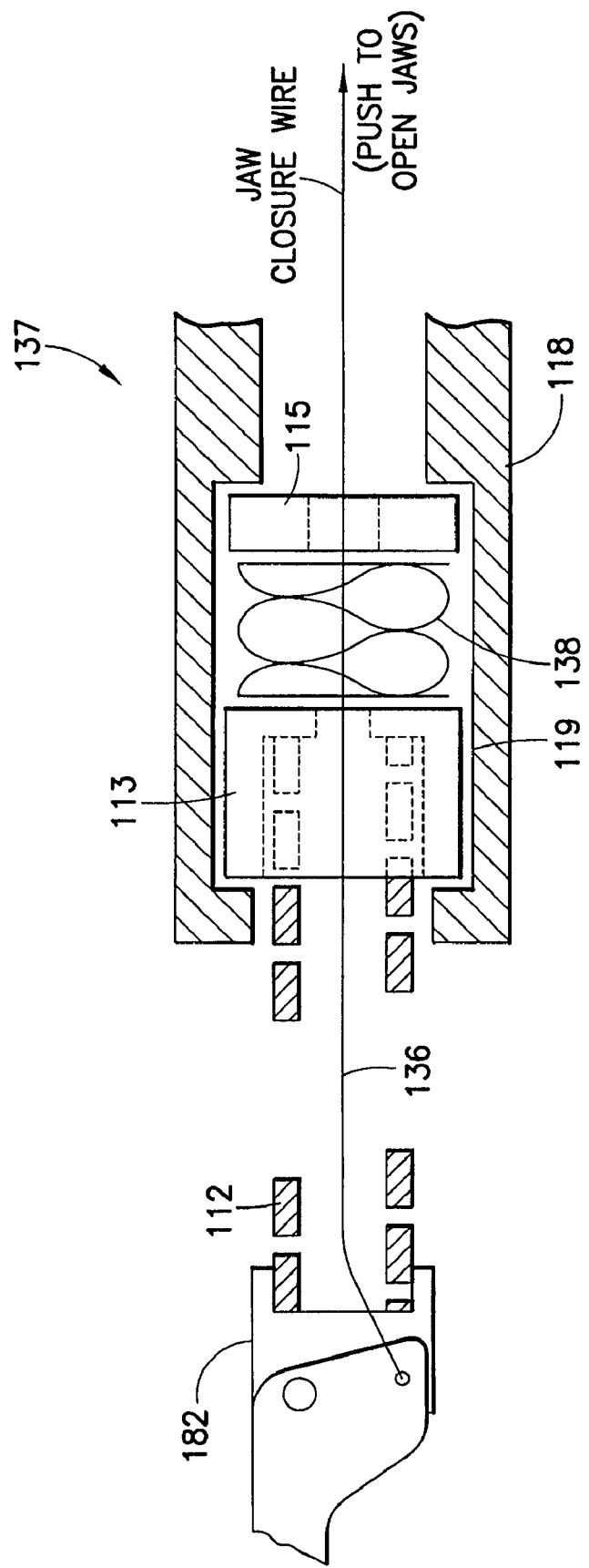
FIG. 4B is a schematic view of a first alternate force absorber arrangement.

FIG. 4B shows a first alternate embodiment of a force limiting mechanism 137. Here, the coil 112 is provided with a proximal bushing 113. The manual actuator or handle 118 is provided with a recess 119 which is dimensioned to receive the bushing 113, a washer/spacer 115, and a compression spring 138 therebetween. Those skilled in the art will appreciate that if, during closing of the jaws, an obstacle prevents the jaws from closing fully, the proximal force applied to the control member 136 will be applied to the distal clevis 182, the coil 112, and the handle 118. The handle will exert an equal and opposite force in the distal direction against the washer/spacer 115. As a result, when the spring force of the compression spring 138 is exceeded, the proximal end of the coil will move the bushing 113 against the spring 138.

Still referring to FIGS. 1-6, and particularly FIG. 4, the crank 26 is coupled to a transmission 46 which is coupled to a second control member 48. More particularly, the transmission includes an input spur gear 47 which is coupled to the crank, a step-up spur gear 49 coupled to the input spur gear, and a crown gear 50 which is coupled to the step-up spur gear. The crown gear engages a pinion 52 coupled to a cylinder 54 having a keyed interior which engages the second control member 48 which is provided with a shepherd's crook 48a (also as illustrated in FIG. 29) at or near its proximal end. The cylinder 54 is mounted on two bearings 55, 57 which are held by clamps 55a, 57a. The second control member 48 (as discussed in detail below with reference to FIGS. 8-11) is threaded along a distal portion thereof. From the discussion which follows, it will be appreciated that the length of the cylinder 54 is sufficient to allow distal movement of the second control member 48 until all of the clips have been dispensed. According to the presently preferred embodiment, the control member 48 is made from 17-7 PH stainless steel wire.

According to the presently preferred embodiment, an energy storing flywheel 56 is coupled to the cylinder 54. Alternatively, the flywheel and cylinder could be a single molded part. The flywheel smoothes the operation of the crank which would otherwise require the application of increasing force through its rotation, as in the beginning of its rotation, the control member is causing a clip to be advanced, whereas at the end of its rotation, the control member is causing the clip to be formed by pushing it against an anvil in the end effectors (as discussed in more detail below). Those skilled in the art will appreciate that in order to be effective, the flywheel is preferably provided with a relatively large rotational mass for energy storage. When the flywheel is spun (rotated) by rotation of the crank, a certain amount of energy is invested which increases the kinetic energy (mass×velocity) of the flywheel. Some of this energy is lost over time to friction; however, some of the energy used to spin the flywheel is stored in the form of kinetic energy. Later, it is possible to retrieve this energy through direct mechanical translation. In the case of the present invention, when the crank 26 is first rotated, the control member 48 offers little resistance (as the clips are moving forward easily) and most of the energy applied to the crank is used to put the flywheel 56 in rotation. Near the end of the crank's rotation, torsional resistance is built up by the control member 48 because it is near the end of the cycle where the clip is being bent into its final shape. At this point, the kinetic energy in the flywheel is released and eases the remainder of the crank cycle. Preferably, according to the invention, the flywheel 56 is chosen so that the force which is applied to the crank 26 is substantially even (e.g., does not change by more than 25%) over the entire movement of the crank 26 necessary to dispense a single clip.

Figure 6:
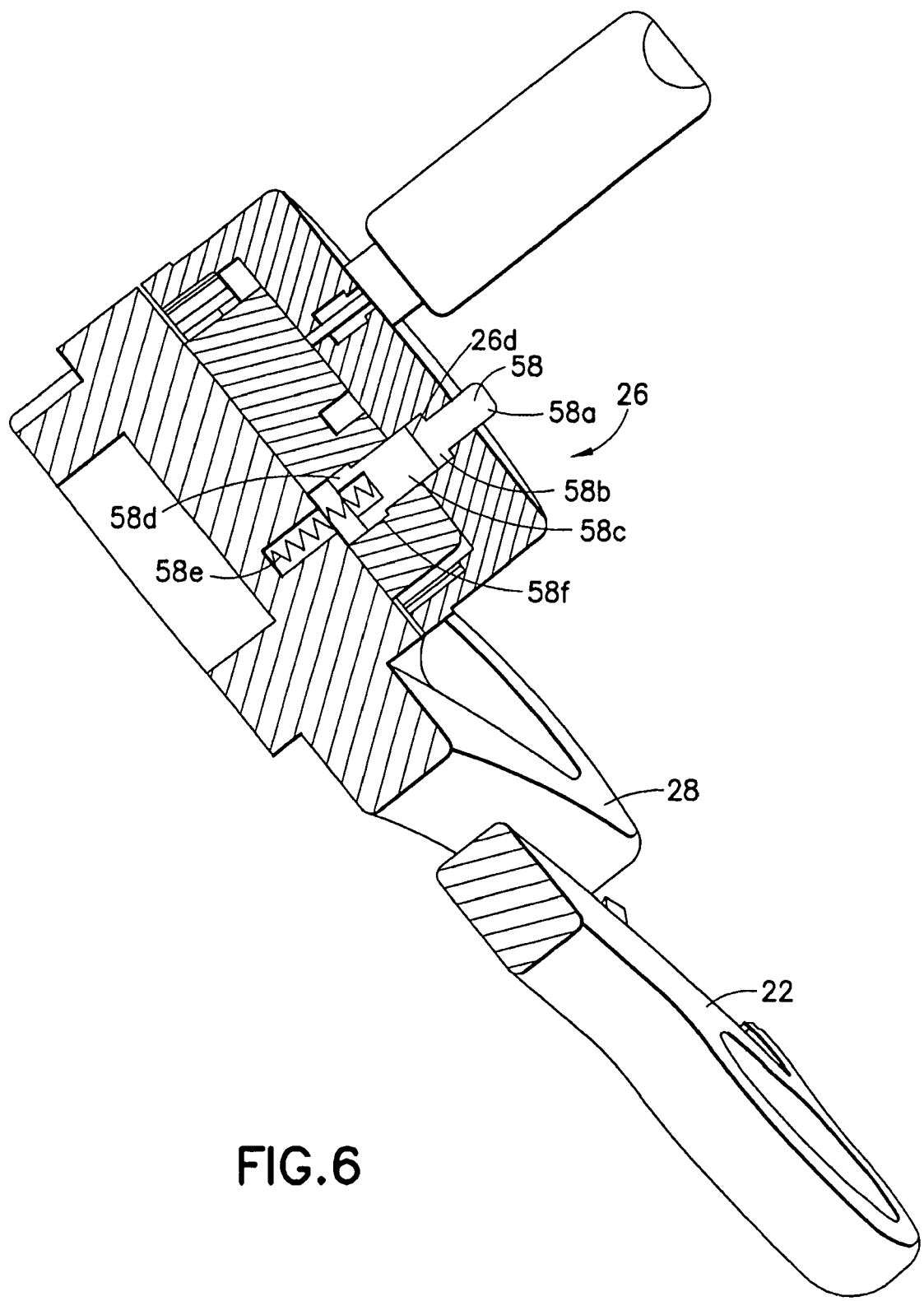
FIG. 6 is a sectional view through the crank illustrating the locking detent.
Figure 7:
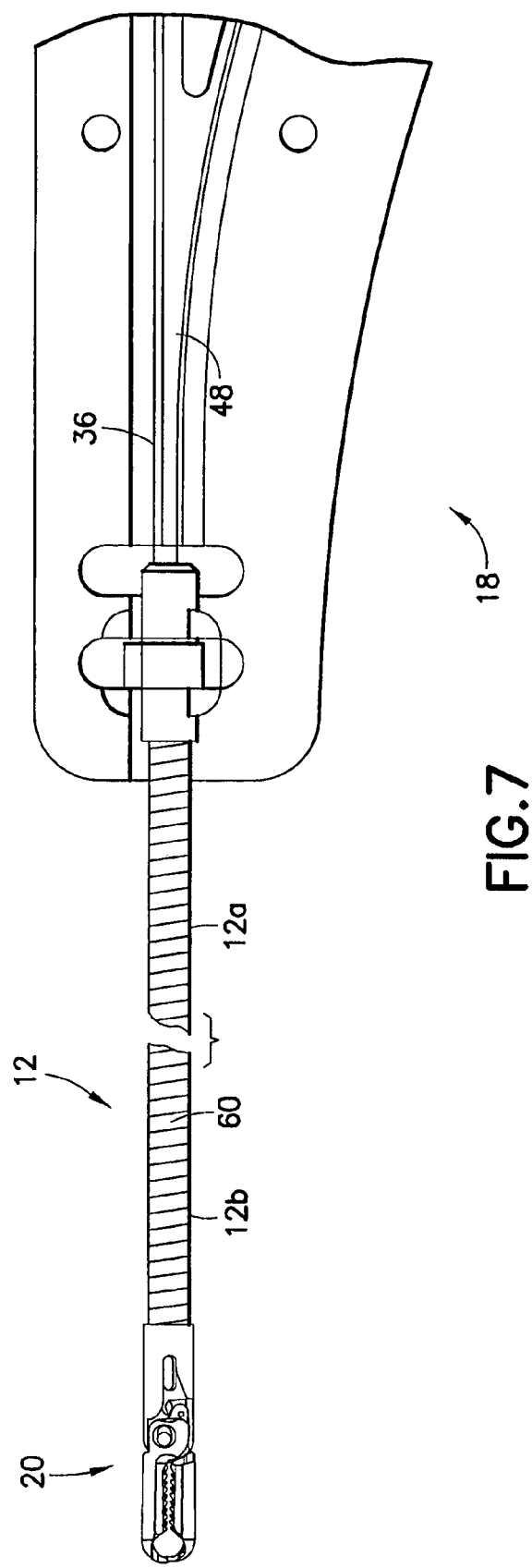
FIG. 7 is a broken partially disassembled view illustrating the coils, the jaws, and the distal end of the manual actuator.

As seen best in FIGS. 5 and 6, the crank 26 is provided with a detent lock 58 which must be released before the crank 26 can be turned and which automatically locks the crank 26 after one rotation. Preferably, the crank 26 is also provided with a ratchet mechanism (not shown) which prevents it from being rotated backwards. The crank is also preferably provided with a lock (not shown) which prevents it from being turned until the jaws are closed. The crank may also be provided with a revolution counter (not shown) which can be coupled to the input spur gear and which counts the number of times the crank has been rotated and thus indicates the number of clips which have been dispensed. The revolution counter may also be used to prevent the crank from rotating after all of the clips have been dispensed. Ideally, the crank is also provided with a lockout mechanism which prevents it from being rotated twice without opening and closing the jaws between rotations of the crank.

According to the embodiment illustrated in FIGS. 5 and 6, the crank 26 has a plurality of spaced apart peripheral finger grips 26a and a knurled outer periphery 26b. The crank handle 26c is optionally removable so that the crank can be rotated like a knob if desired. The detent lock 58 includes a push button 58a having a flange 58b, a lock pin 58c having a flange 58d and a spring 58e. The lock pin 58c is disposed in a stepped bore 58f and is biased by the spring 58e into the stepped bore 26d in the crank 26. When the button 58a is pressed, the lock pin 58c is moved against the spring 58e and out of the bore 26d, freeing the crank to rotate.

According to an exemplary embodiment, the transmission causes the second control member to be rotated 58.1875 revolutions when the crank is turned one revolution. The pitch of the threads on the control member result in the control member advancing 0.285 inches when the crank is turned one revolution. The gears and the thread pitch are selected for a particular clip length. According to the presently preferred embodiment, it is only necessary to change the crown gear (by increasing or decreasing the number of teeth) to accommodate clips of different length.

As illustrated in FIGS. 1-4 and 4a, the distal end of the manual actuator 18 has a pair of vertical slots 15 which capture a coil connector (not shown) that is attached to the proximal end of the coil.

The Control Members

Referring now to FIGS. 7-10, the control members 36, 48 extend through a flexible coil 12 coupled to the distal end of the manual actuator 18. According to the invention, the coil 12 has two parts: a proximal part 12a and a distal part 12b which are coupled to each other by a rigid member 60. The rigid member 60 is substantially cylindrical having a center portion 60-1 of larger diameter than the end portions 60-2, 60-3. The end portions 60-2, 60-3 are dimensioned to fit inside the coils 12a, 12b and the central portion 60-1 is dimensioned to have an outer diameter substantially the same as the outer diameter of the coils 12a, 12b. The rigid member 60 has four bores 60a-60d. One of the bores, 60d, is threaded and engages the threaded portion of the second control member 48. Because the rigid member 60 is fixed relative to the coils 12a, 12b, it will be appreciated that this threaded engagement causes the second control member 48 to move distally through the rigid member 60 when it is rotated by the crank 26 (FIG. 2).

Two of the other holes, 60a and 60b, in the rigid member 60 allow the passage of a pair of pull wires 62, 64 which are described in more detail below with reference to FIGS. 16 and 17. The proximal ends of the pull wires are coupled to a joiner 66 which has four bores 66a-66d. One pull wire is coupled to bore 66a and the other is coupled to bore 66b. The first control member 36 extends through and is coupled to the bore 66c, and the threaded control member 48 freely passes through the bore 66d. In this manner, longitudinal movement of the first control member 36 causes longitudinal movement of the pull wires 62, 64. The portion 36a of the control member 36 which extends through the joiner 66 extends into the bore 60c of the rigid member 60. The length of this portion 36a is sufficient to engage the bore 60c throughout the range of movement of the control member 36. In this manner, rotation of the control member 36 with the knob 24 (FIG. 1) causes rotation of the rigid member 60 which causes rotation of the distal portion 12b of the coil 12 which results in rotation of the jaws 20 and the store of clips about the longitudinal axis of the coil.

Figure 8:
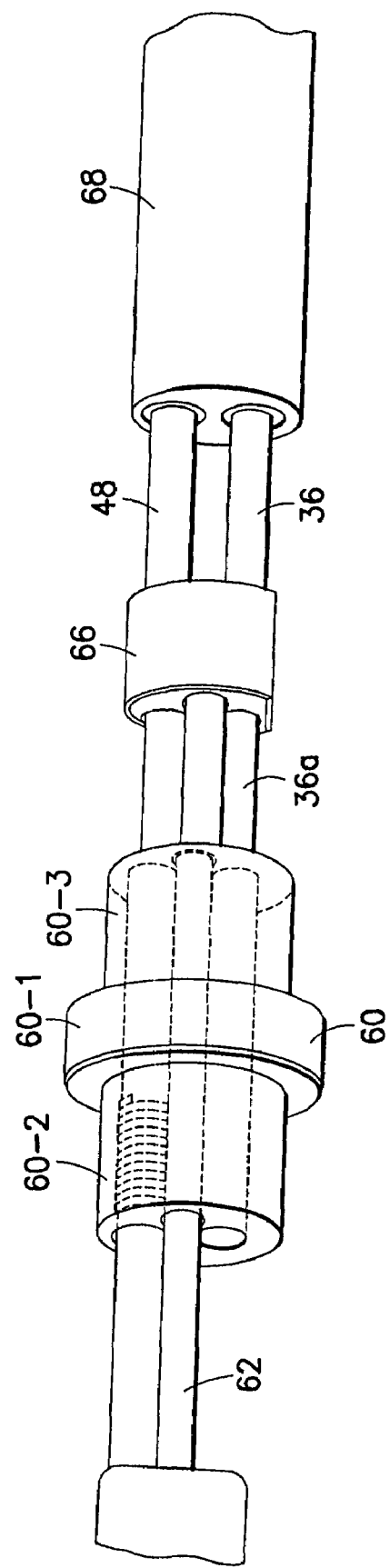
FIG. 8 is a broken partially transparent perspective view of the control members, the joiner, the rigid member, one of the pull wires, the pusher, a portion of the garage and a portion of a clip.
Figure 9:
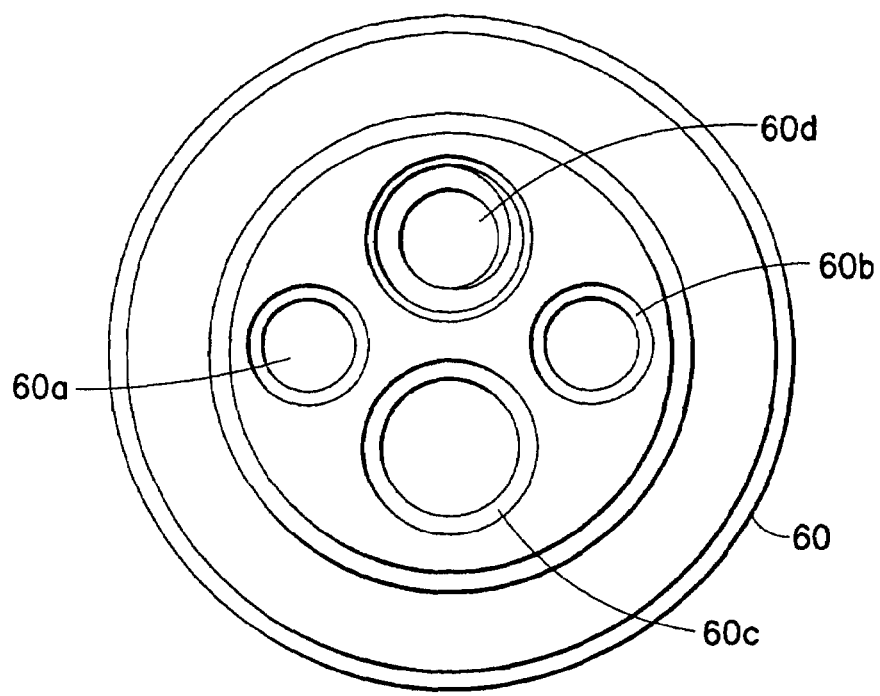
FIG. 9 is a plan view of the rigid member.
Figure 10:
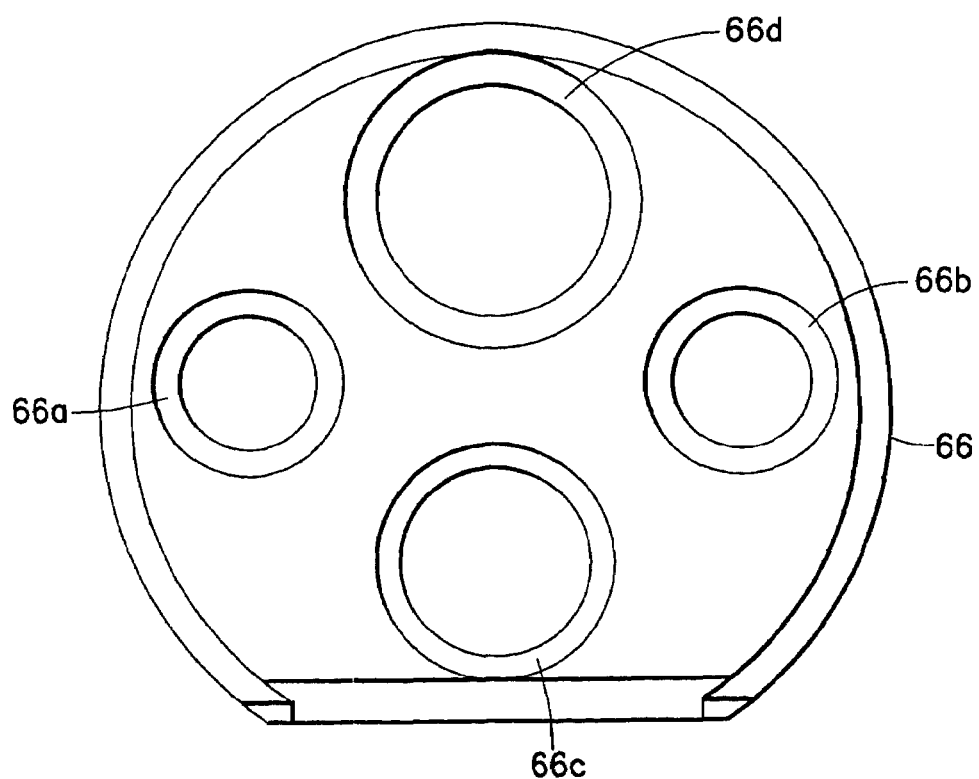
FIG. 10 is a plan view of the joiner.

As seen best in FIG. 8, the control members 36 and 48 are protected by a dual lumen flexible sheath 68 inside the proximal portion 12a of the coil 12. The sheath 68 reduces friction between the control members and the interior of the coil. The sheath 68 also prevents buckling or kinking of the control members. It should also be noted that a friction-reducing sheath is preferably provided along the entire exterior surface of the coil to reduce friction between the coil and the lumen of the endoscope through which it is delivered and to protect the lumen of the endoscope from damage.

According to a presently preferred embodiment, both control members have smaller diameters in their distal portions to add flexibility and larger diameters in the proximal portions to optimize torque transmission.

The Pusher

Figure 11:
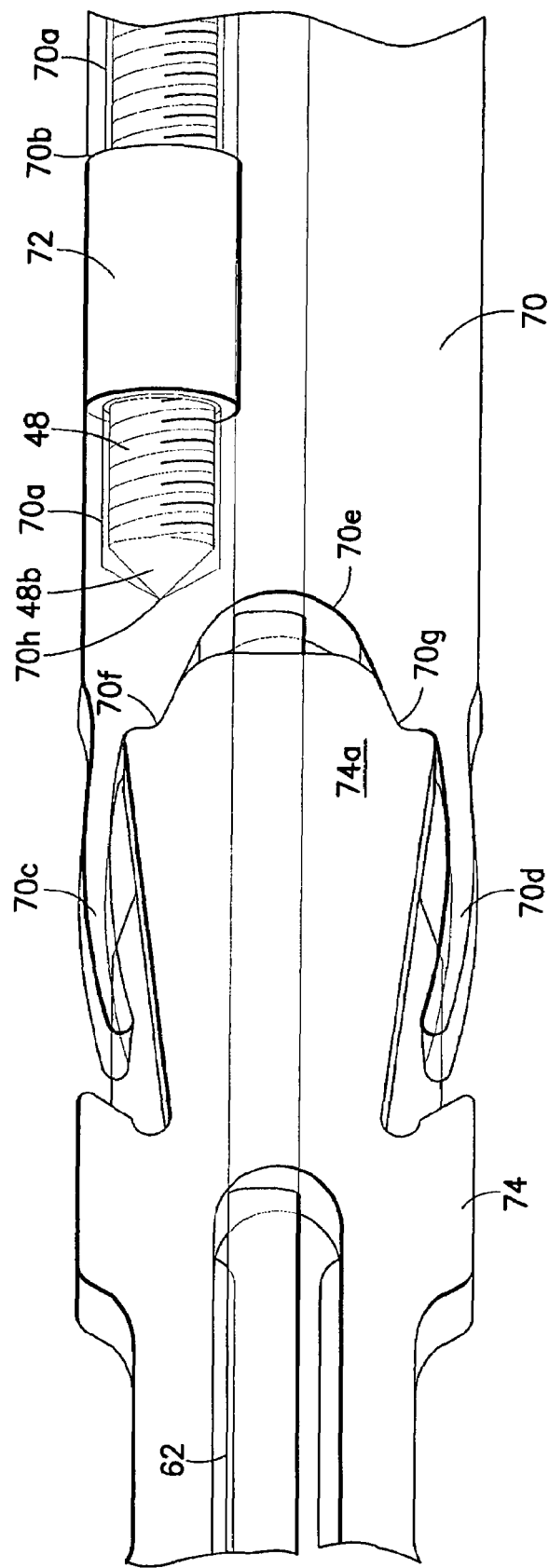
FIG. 11 is a broken partially transparent perspective view of the threaded control member, the pusher, a portion of a clip, and one of the pull wires.
Figure 12:
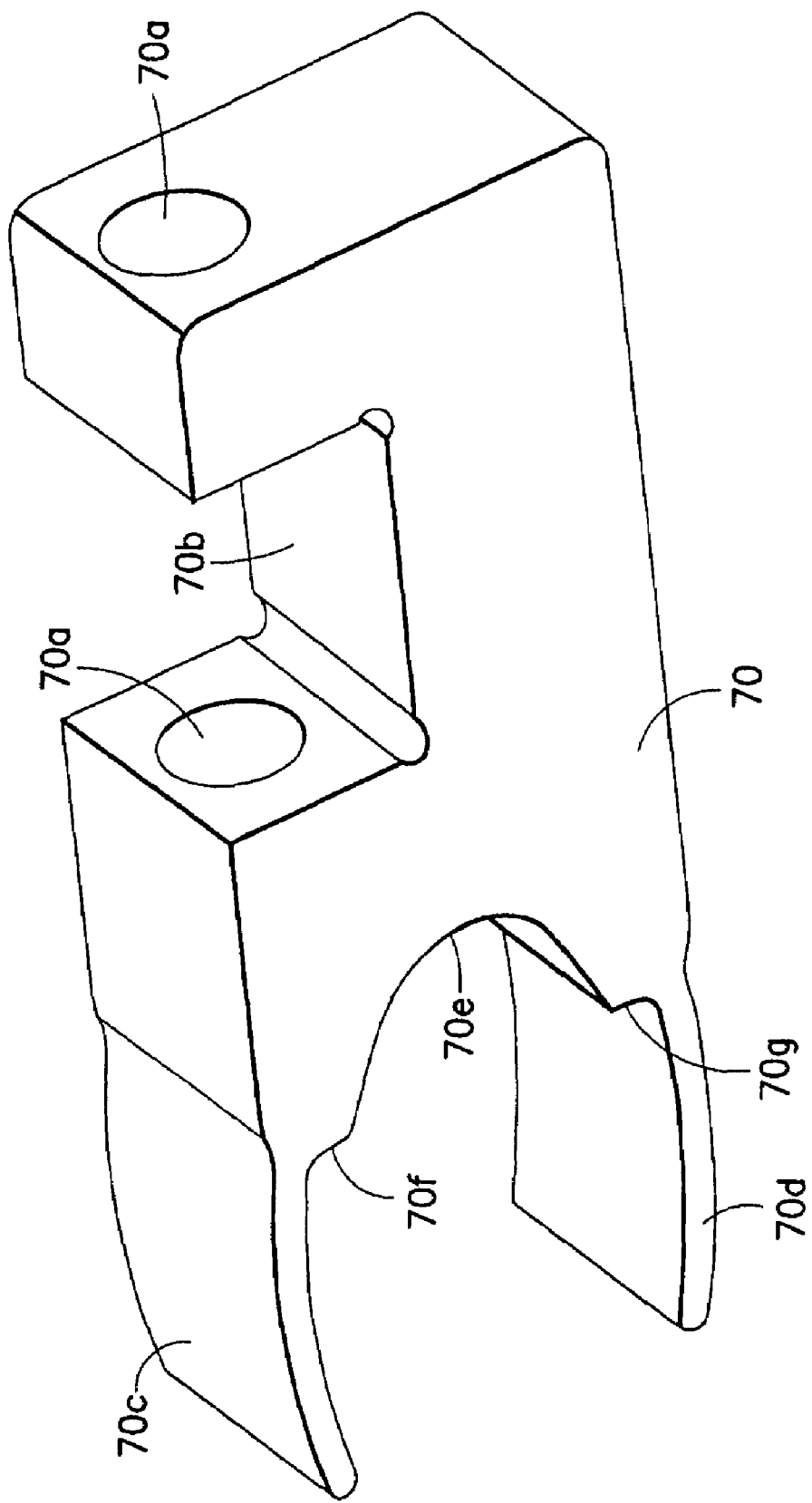
FIG. 12 is a perspective view of the pusher.
Figure 13:
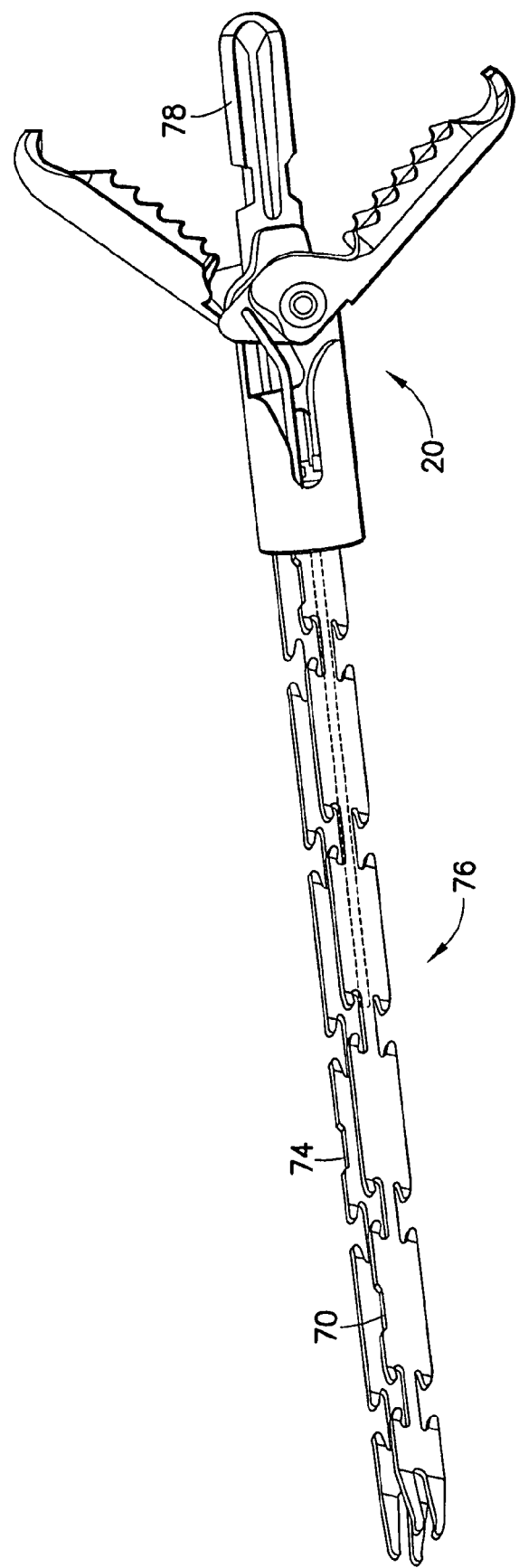
FIG. 13 is a partially cut away perspective view of the garage, the clevis, the jaws and a clip in the applied configuration.
Figure 14:
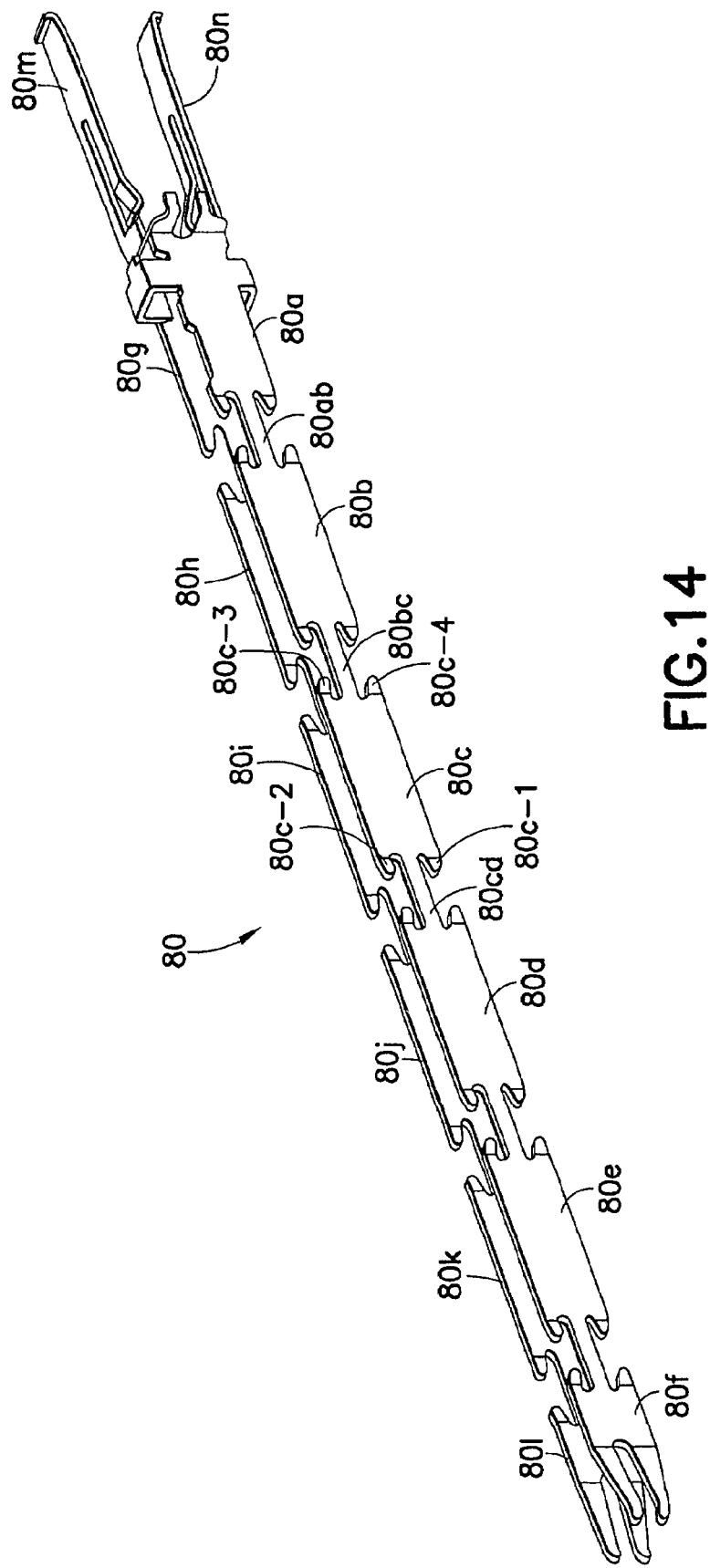
FIG. 14 is a perspective view of the garage.

Turning now to FIGS. 11-13, the distal end of the threaded control member 48 is coupled to a clip pusher 70. As seen best in FIG. 12, the pusher 70 is a generally rectilinear member having an off-axis bore 70a intersected by a notch 70b. A pair of inwardly curved distally extending fingers 70c, 70d are separated from a distal mouth 70e by shoulders 70*f*, 70*g*. As seen best in FIG. 11, the distal end of the threaded control member 48 extends through the bore 70*a* and is coupled to a cylinder 72 which is captured in the notch 70*b*. The cylinder 72 may be crimped or welded to the control member 48. The coupling of the pusher and the control member is such that the control member can freely rotate relative to the pusher. As seen best in FIG. 11, the distal end 48*b* of the control member 48 is sharpened to a point and the distal end of the throughbore 70*a* is provided with a conical wall 70*h*. The apex angle of the conical wall 70*h* is larger than the apex angle of the point 48*b*. From the foregoing, those skilled in the art will appreciate that when the control member 48 is rotated, it moves distally, pushing the pusher distally. It will also be appreciated that the frictional engagement of the control member 48 with the pusher 70 is limited to the small area of engagement of the point 48*b* with the apex of the cone 70*h*.

As seen best in FIG. 13, the clip pusher 70 is arranged adjacent to the proximally closest clip 74 in the store of clips 76 which are axially arranged one after the other proximal to the jaw assembly 20. When the control member 48 is translated distally, the store of clips 76 is moved distally until the ultimate clip 78 (the one at the distal end of the store) enters the closed jaws and is applied to tissue through the bending of its ends by the interior anvils of the jaws. FIG. 13 shows the jaws open after the clip 78 was applied.

As seen best in FIG. 11, the clip 74 (which is identical to all of the other clips) has a proximal tail 74*a* which is engaged by the mouth 70*e* and shoulders 70*f*, 70*g* of the pusher 70. The fingers 70*c* and 70*d* constrain the clip from vertical movement and allow the pusher to lightly grab the clip, which facilitates clip loading during assembly. Additional details of the clip may be appreciated upon review of previously incorporated U.S. Ser. No. 10/867,412.

Those skilled in the art will appreciate that the arrangement of threads could be changed while still achieving the same or similar results. For example, rather than arranging the threaded control member to advance distally, threads could be supplied on the pusher with the threaded control member being translationally stationary. In this arrangement, rotation of the threaded control member causes the pusher to be translated along the control member.

The Garage

Figure 15:
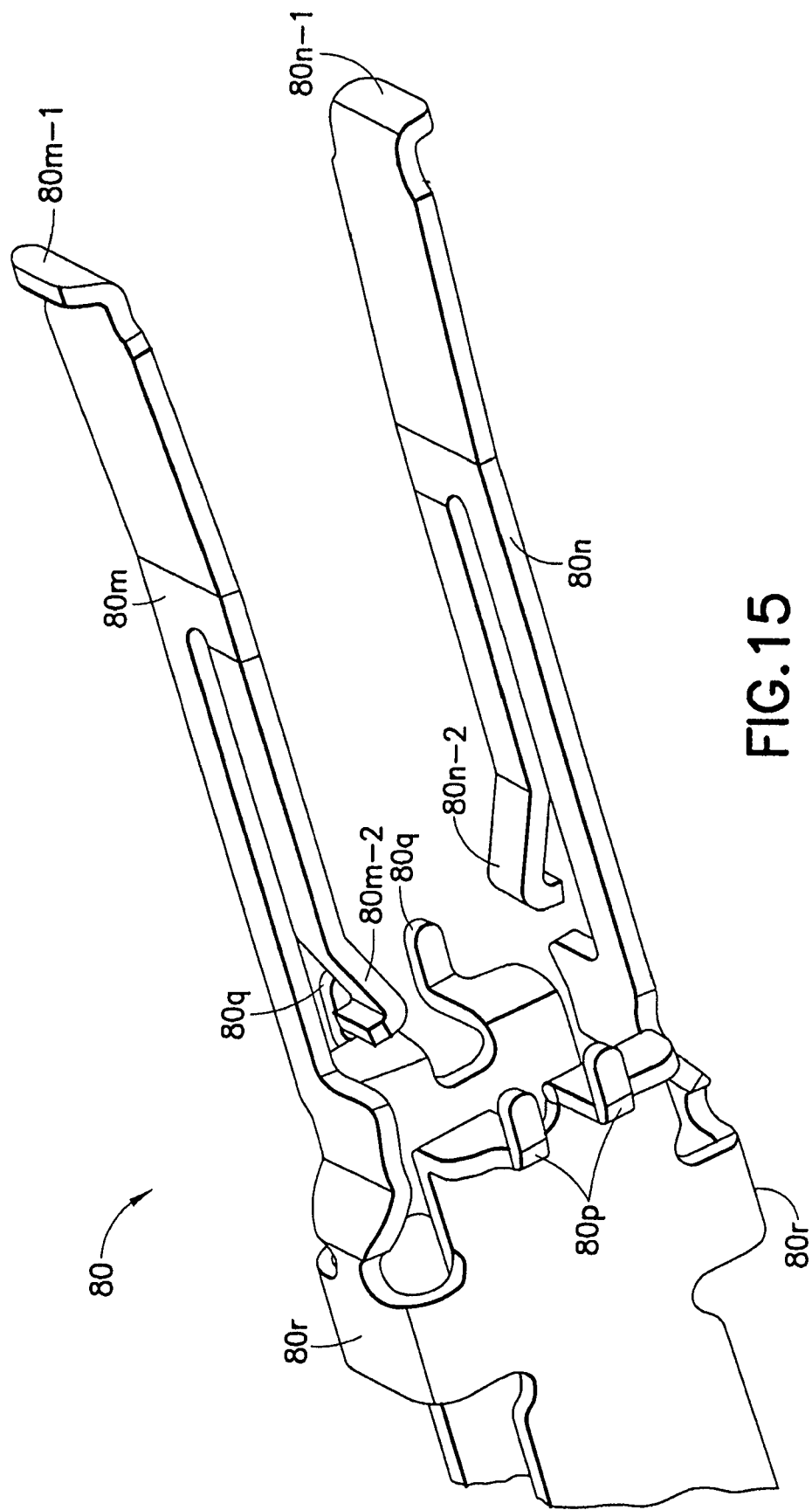
FIG. 15 is an enlarged broken perspective view of the distal end of the garage illustrating the biased stops.
Figure 16:
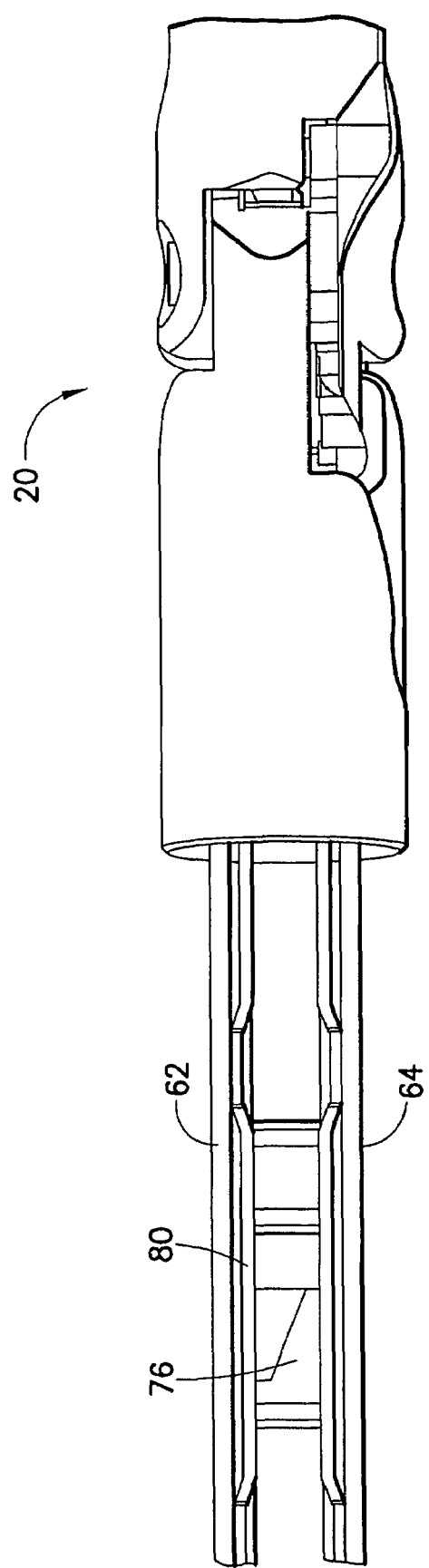
FIG. 16 is a broken plan view illustrating the clevis and portions of the jaws, pull wires, garage, and clips.

As seen best in FIGS. 13 and 16, the store of clips 76 is housed in a garage 80 inside the distal portion 12*b* of the coil 12 proximal to the jaw assembly 20. Details of the garage 80 are seen in FIGS. 14-17. The garage 80 generally comprises a plurality of parallel side walls 80*a*-80*l* and pair of distally extending fingers 80*m*, 80*n* which are orthogonal to the side walls. Each side wall has a plurality of outwardly directed spacers, e.g. 80*c*-1, 80*c*-2, 80*c*-3, 80*c*-4. These spacers engage the interior of the coil and assure space between the coil and the garage for the passage of the pull wires 62, 64 (see FIG. 16). Formation of the outwardly directed spacers results in narrow strips, e.g. 80*ab*, 80*bc*, 80*cd*, etc., which add flexibility to the garage. The flexibility at the distal end of the instrument can be important in cases where the endoscope is retroflexed. As seen best in FIG. 16, when the clips are arranged in the garage, the abutment of one clip against another lies in this narrowed region. Thus the clips can flex at their abutment.

As seen best in FIG. 15, the distally extending fingers 80*m*, 80*n* each have an outwardly extending distal lip 80*m*-1, 80*n*-1 and an inwardly extending proximal stop 80*m*2, 80*n*-2. The fingers 80*m*, 80*n* help orient the garage relative to the clevis. The distal lips help the garage engage the clevis as described below and the proximal stop's prevent unwanted movement of the penultimate clip as described below. Opposite pairs of parallel fingers 80*p* and 80*q* are arranged in spaced apart planes orthogonal to the planes of the fingers 80*m*, 80*n*. These fingers 80*p*, 80*q* extend from a proximal collar 80*r* and engage the clevis as seen best in FIG. 17, described in detail below.

According to the presently preferred embodiment, the garage is made from a single piece of stamped and folded stainless steel.

Unlike our earlier clip appliers, there is no need to chain the clips together so that they can be pulled back. There is also no need to pull any of the clips back at any time.

The Jaw Assembly

Figure 17:
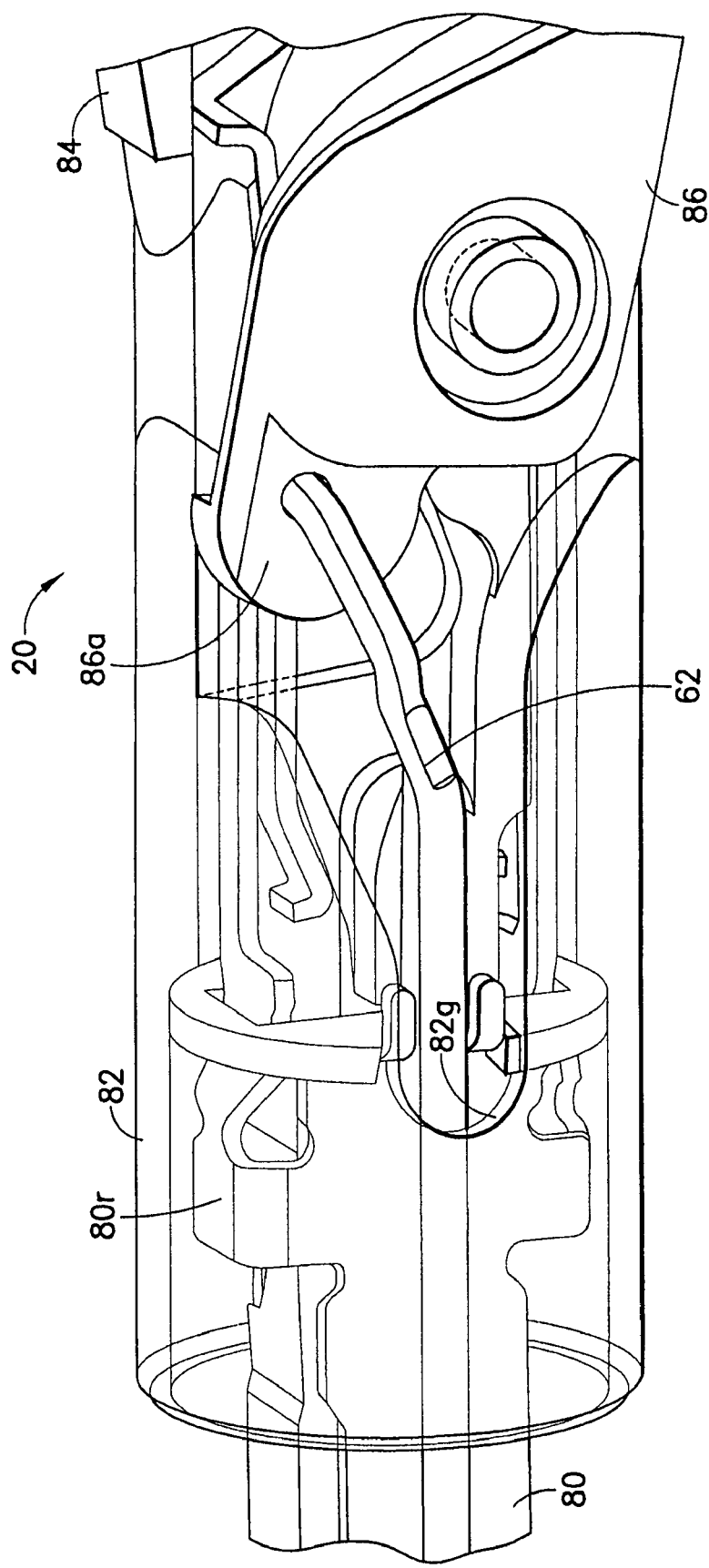
FIG. 17 is a broken partially transparent perspective view illustrating the clevis and portions of the jaws, pull wires, garage, and clips.
Figure 18:
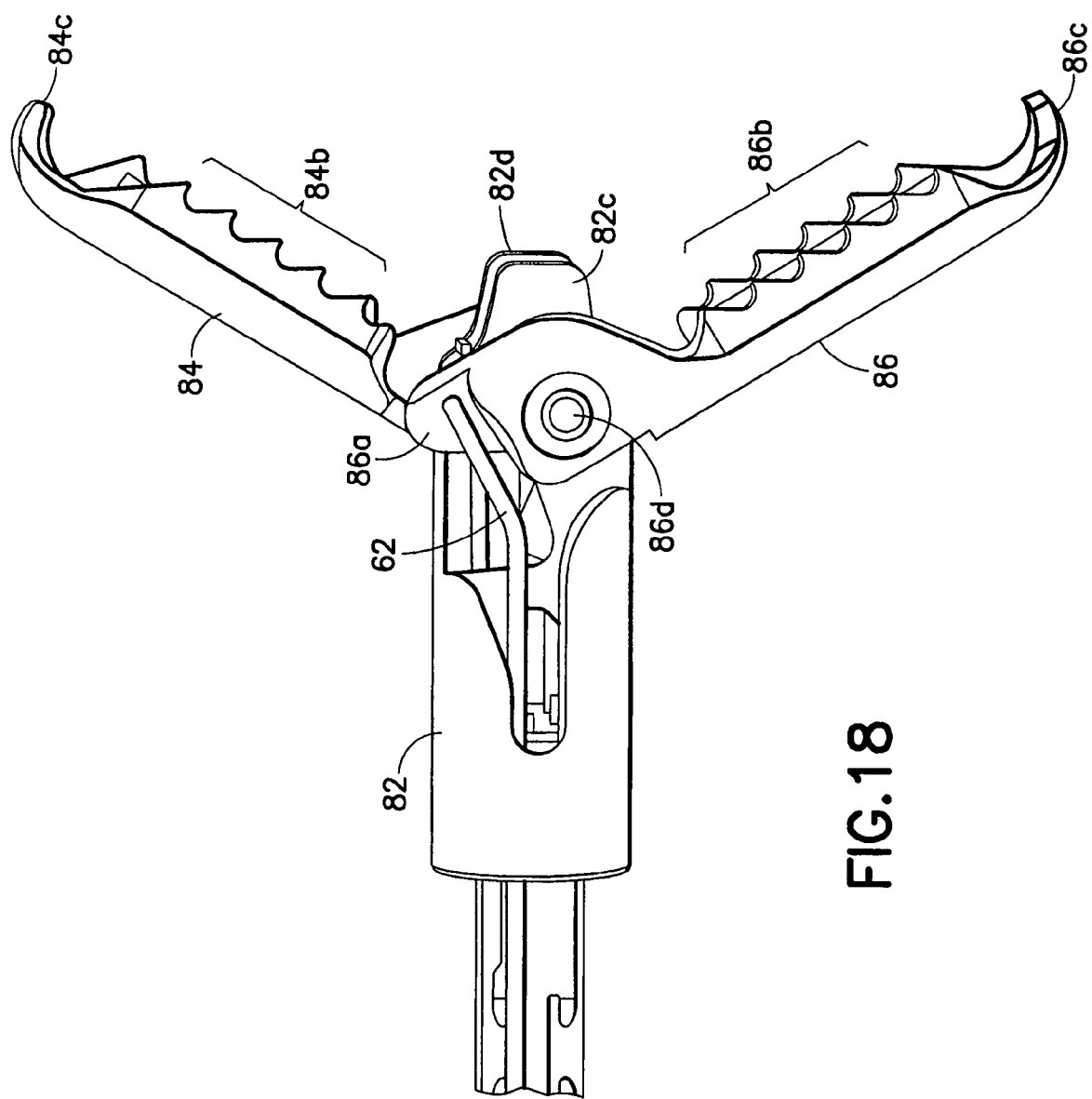
FIG. 18 is a broken perspective view of the clevis, open jaws and portions of a pull wire and garage.
Figure 19:
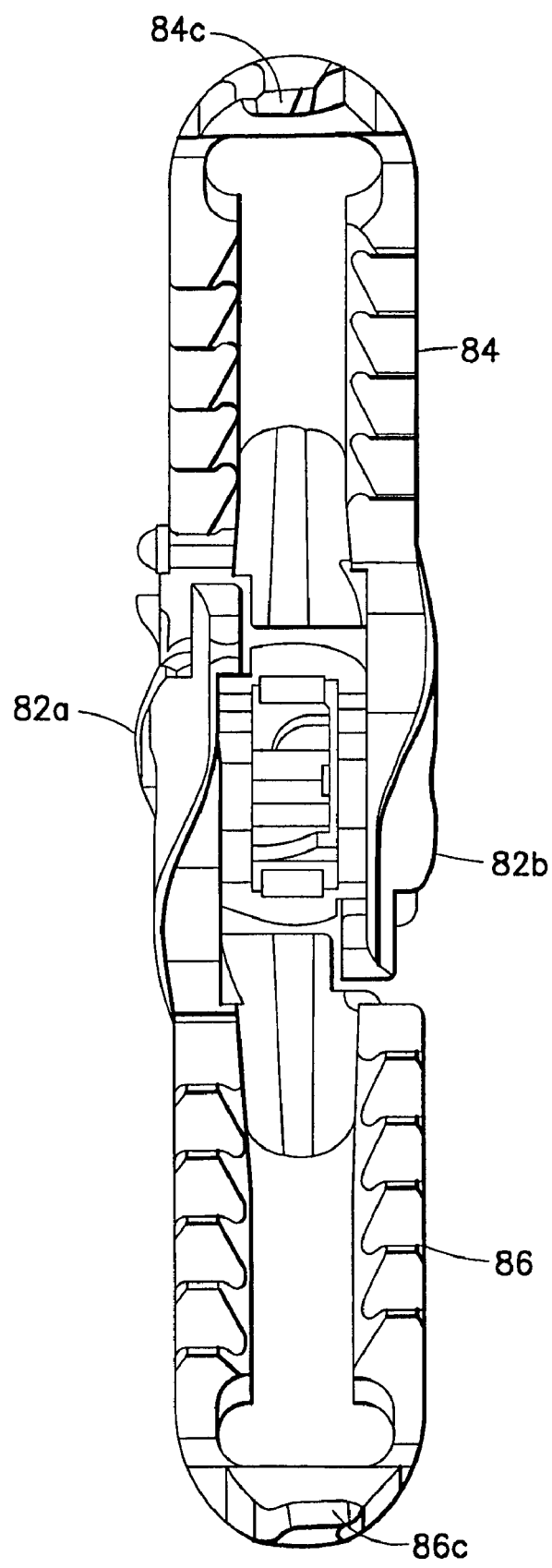
FIG. 19 is a distal end view looking into the open jaws.
Figure 20:
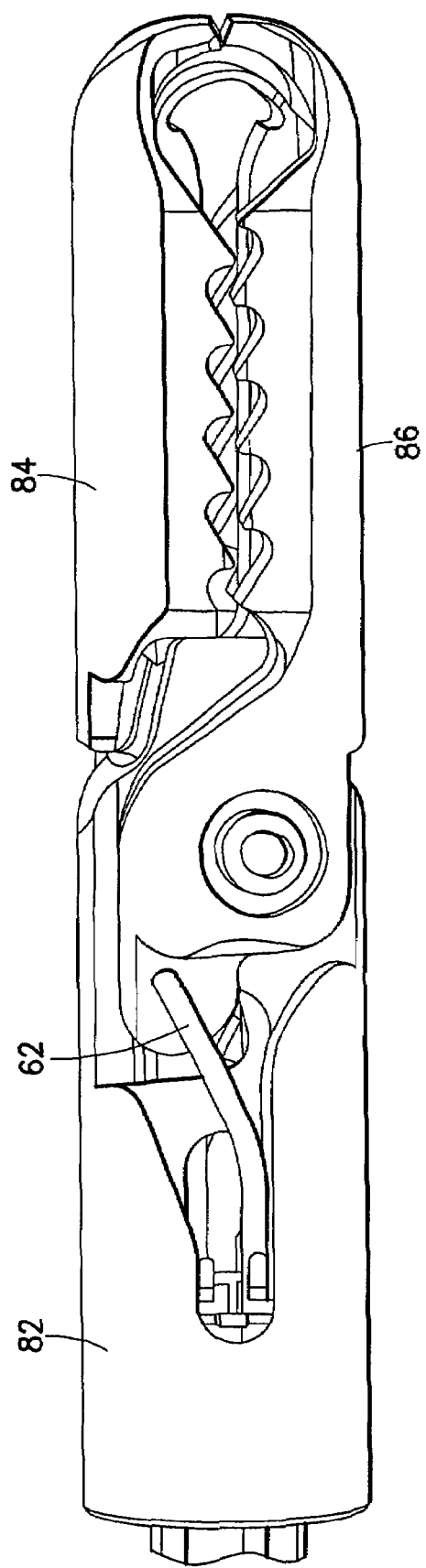
FIG. 20 is a broken side elevational view of the clevis, closed jaws, and an applied clip.
Figure 21:
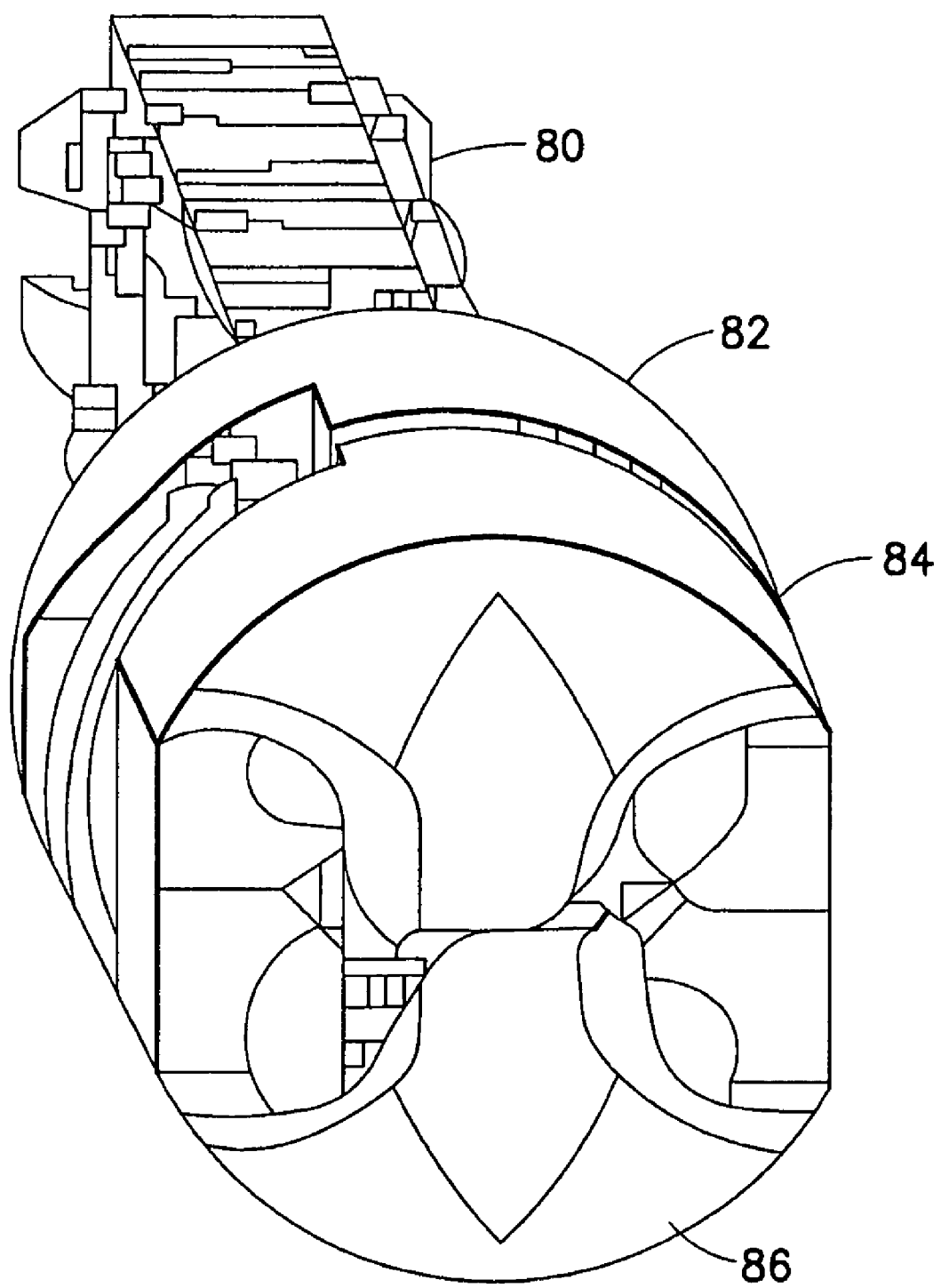
FIG. 21 is a perspective end view of the closed jaws, clevis, and the garage.
Figure 22:
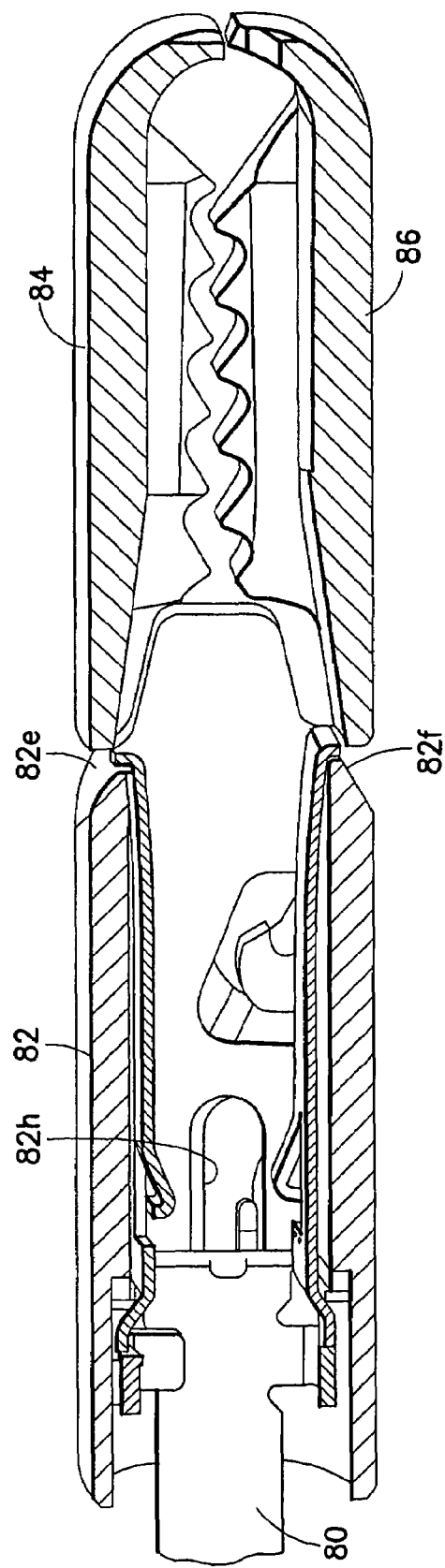
FIG. 22 is a broken longitudinal section illustrating the jaws closed, the clevis and a distal portion of the garage, with no clips.

FIGS. 17-27 illustrate details of the jaw assembly 20 which includes a clevis 82 and a pair of jaws 84, 86. The jaws are hermaphroditic mating jaws, i.e. the jaws are identical and arranged to mate with each other. Each has a proximal tang 84*a*, 86*a*, a plurality of side teeth 84*b*, 86*b*, which are offset one half pitch from each other on opposite sides of the longitudinal axis of the jaw, a distal tooth 84*c*, 86*c*, and a mounting hole 84*d*, 86*d*. The jaws are coupled to the clevis via their mounting holes. As seen best in FIG. 27, the clevis 82 has two off-axis bosses 82*a*, 82*b* upon which the jaws are mounted and held in place by rivets. The distal ends of the pull wires 62, 64 are bent into dogs-legs which are coupled to respective tangs 84*a*, 86*a* of the jaws. It will thus be appreciated that distal movement of the pull wires will cause the jaws to open as shown in FIGS. 18 and 19 and proximal movement of the pull wires will cause the jaws to close as shown in FIGS. 20 and 21. The use of offset bosses increases the mechanical advantage of the jaws. The clevis also is provided with a pair of stops 82*e*, 82*f* (best seen in FIG. 26) which engage ears 84*a*-1, 86*a*-1 on the tangs of the jaws and which allow the jaws to be deflected 45-60 degrees off axis when they are closed and which also allows for an approximately ten degree over-rotation of the jaws. This allows the closed jaws to traverse a tortuous path through the lumen of an endoscope.

As seen best in FIG. 19, the proximal tang and the distal tooth of each jaw lie on opposite sides of the longitudinal axis of the jaw assembly. This arrangement provides stability to the end effector arrangement. In particular, there is a certain amount of clearance between the jaws and the clevis so that the jaws can rotate easily open and closed. This clearance may allow the jaws to rock horizontally on the clevis creating the possibility of jaw misalignment. In the illustrated embodiment, the jaws are forced toward each other horizontally as they are being closed rather than away from each other. This is because the forming anvils act in opposition to the horizontal moments generated by the pull wires.

Figure 23:
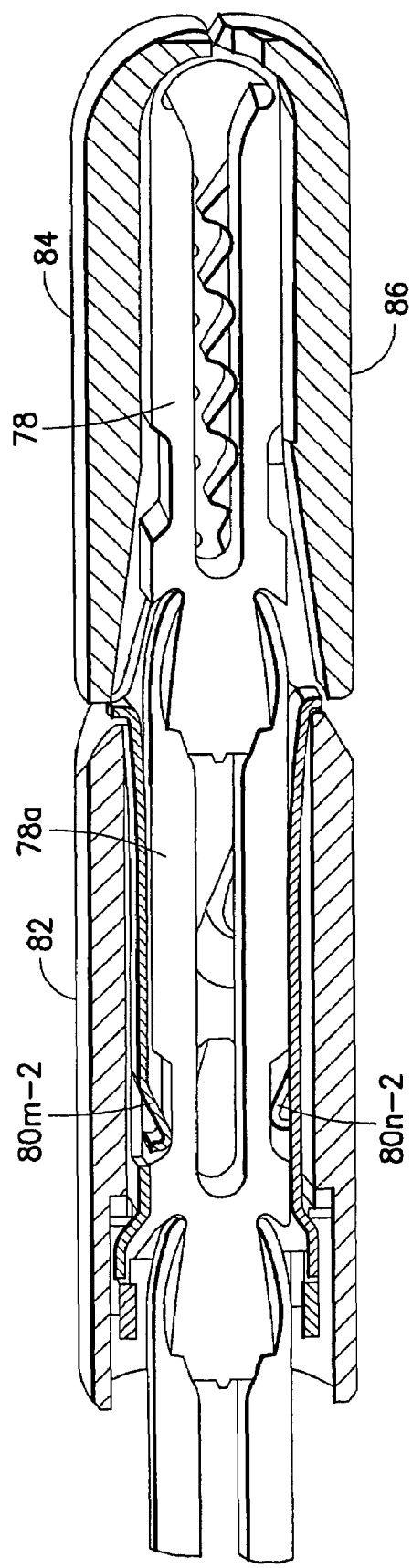
FIG. 23 is a view similar to FIG. 22 but with three clips.
Figure 24:
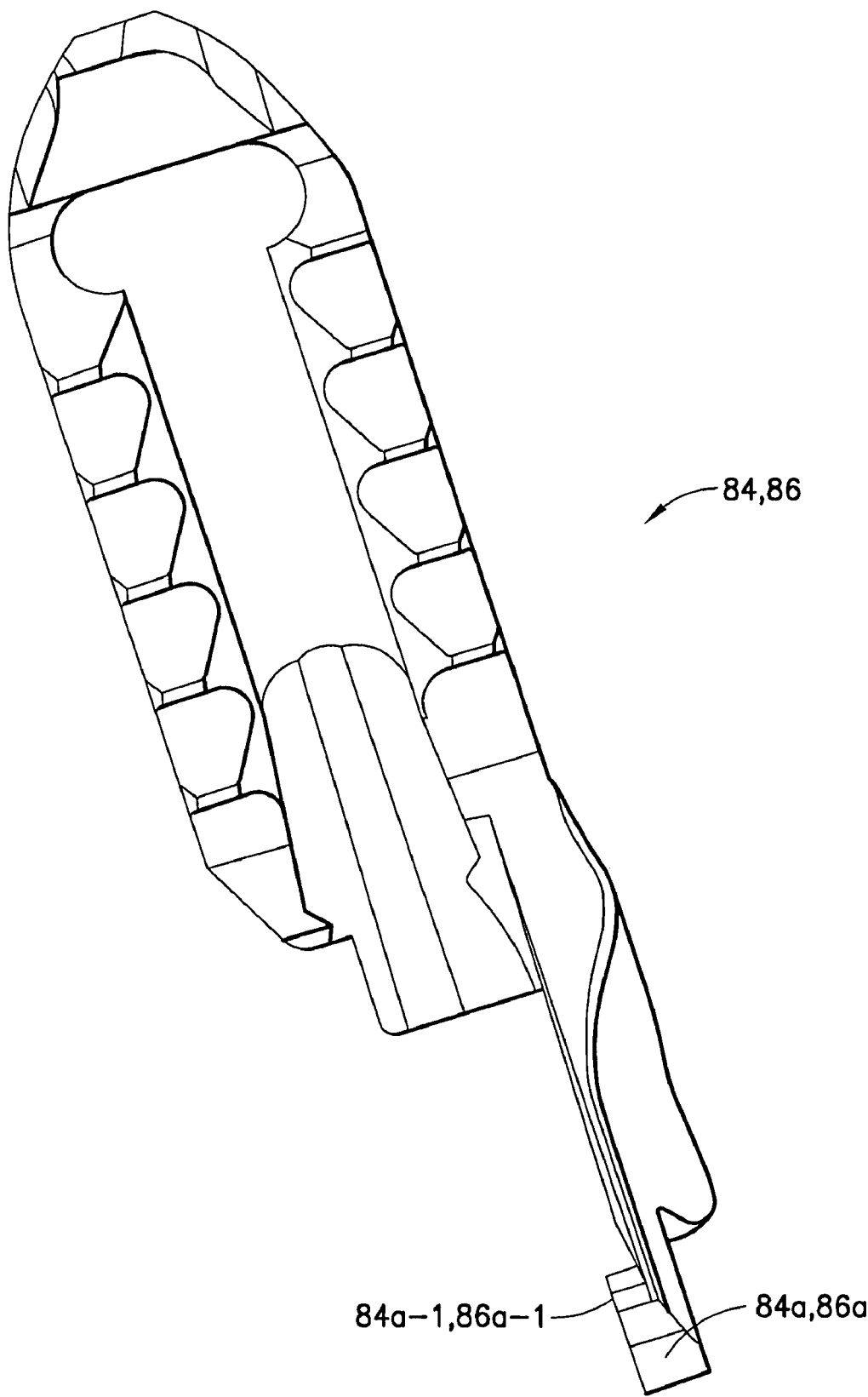
FIG. 24 is a plan view of the interior of a jaw.
Figure 25:
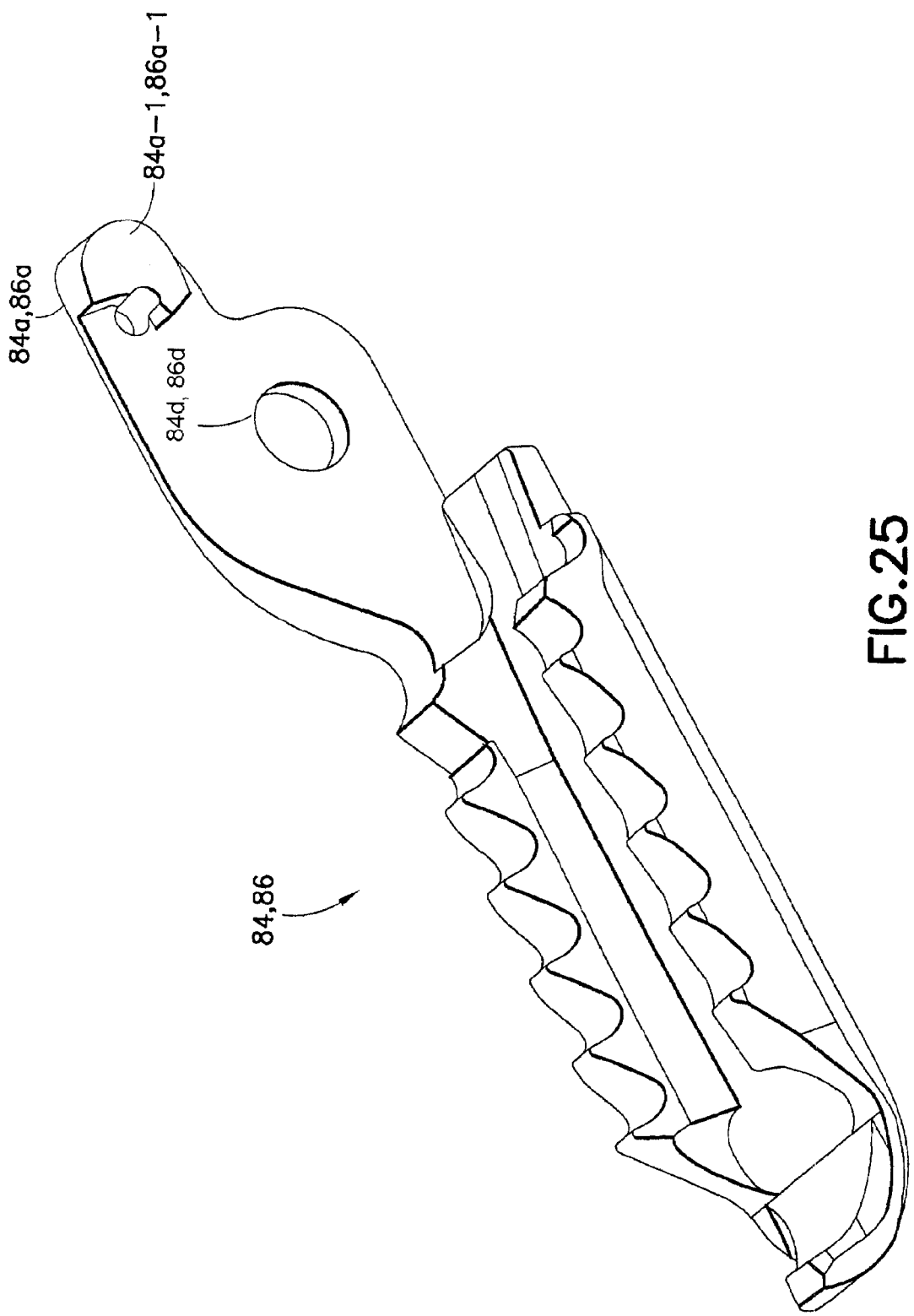
FIG. 25 is a perspective view of the interior of a jaw.
Figure 26:
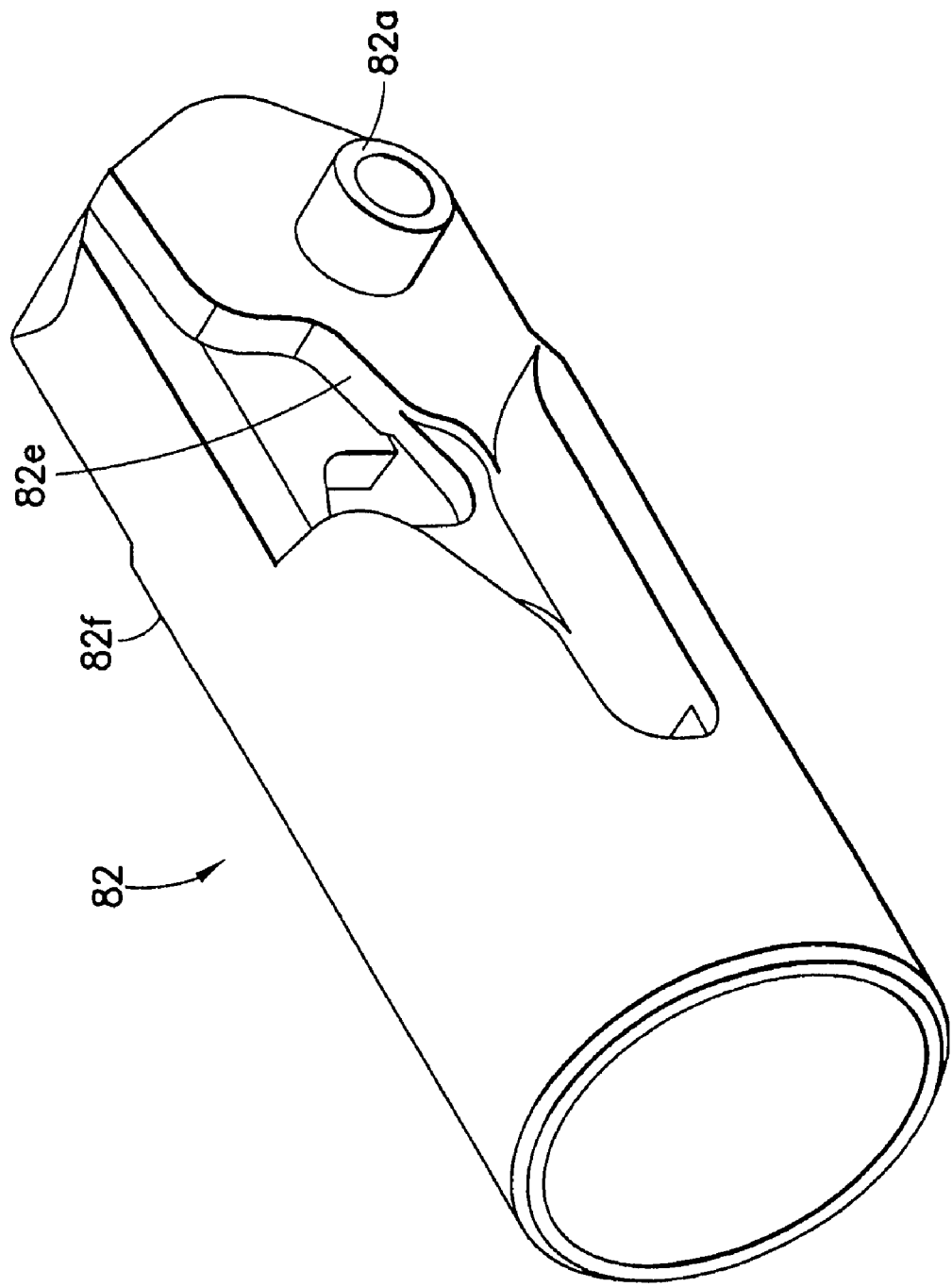
FIG. 26 is a side elevational view of the clevis.
Figure 27:
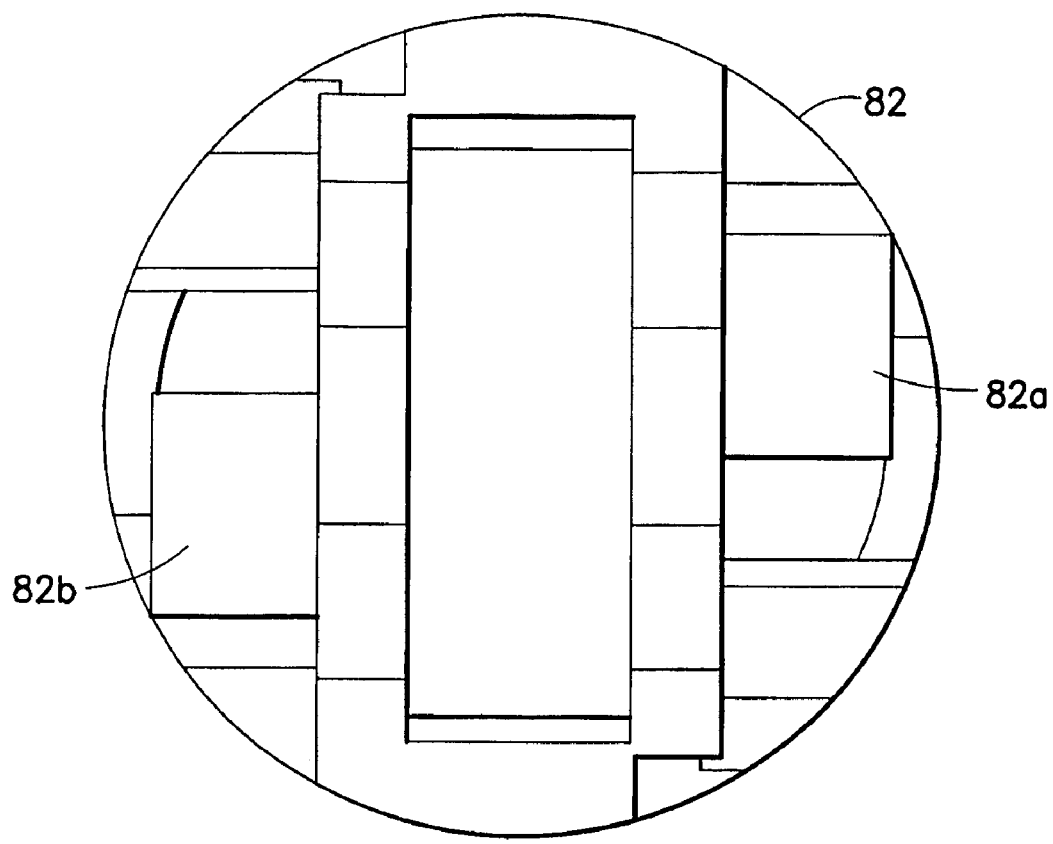
FIG. 27 is a distal end view of the clevis.

The interior surfaces of the distal teeth are forming anvils which cause the two tines of the clip to be bent through approximately 90-180° as shown in FIGS. 20 and 23. In particular, as seen in FIGS. 19 and 21, the distal teeth define two curvature paths, parallel to each other. This allows the two tines of the clip to be bent into parallel semi-circles. The distal teeth also function as a tissue fixation point indicator as the point(s) where the teeth meet are adjacent the location where the tines of the clips pierce the tissue.

As seen best in FIG. 23, after the distal-most (ultimate) clip 78 has been applied, the adjacent or penultimate clip 78*a* is held by the stops 80*m*-2 and 80*n*-2 in the garage 80 and the tines of the clip 78*a* embrace the tail of the clip 78. When the jaws are opened, the jaw assembly can be moved away from the ultimate clip 78 without releasing the penultimate clip 78*a*. As seen best in FIG. 18, with the jaws open, the tines of the penultimate clip 78*a* are shielded by distal fins 82*c*, 82*d* of the clevis 82. However, if the clevis is dimensioned differently, these fins 82*c*, 82*d* are not necessary because the tines of the clip will not extend out of the clevis until it is being applied. Other illustrations of the clevis (e.g. FIG. 26) do not show the fins.

As shown in FIG. 17, the garage mates with the clevis in three places in order to secure the garage relative to the clevis. A distal mating is obtained with distal lips 80*m*-1 and 80*n*-1 engaging lips 82*e* and 82*f* of clevis 82 (shown best in FIG. 22). A proximal mating is obtained with fingers 80*p* and 80*q* engaging lateral recesses or bores 82*g*, 82*h*. The third mating is provided by sandwiching the proximal collar 80*r* between the clevis core and the distal end of the coil.

Alternate Embodiment, Self-Pushing Clip

Figure 28:
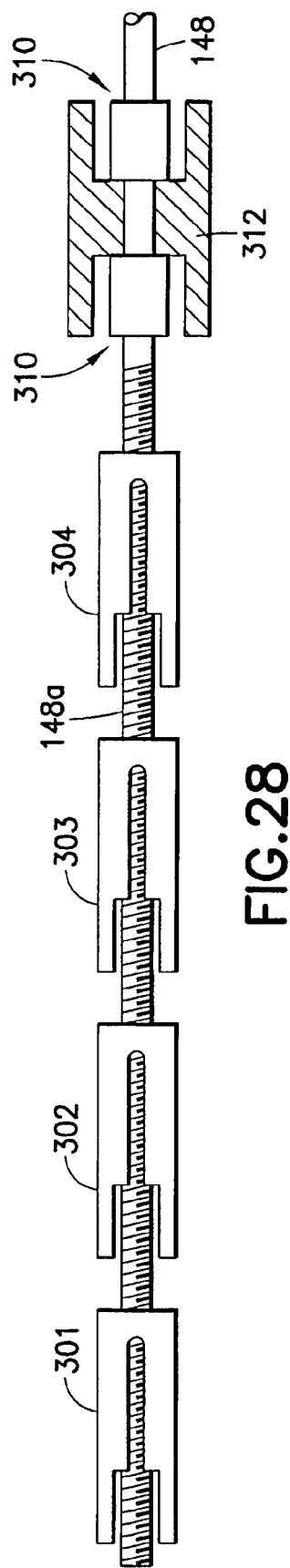
FIG. 28 is a schematic side elevation view in partial section of an alternate embodiment of "self-pushing" threaded clips coupled to a threaded control member.
Figure 28B:
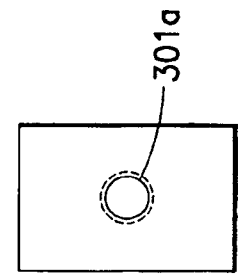
Figure 28A:
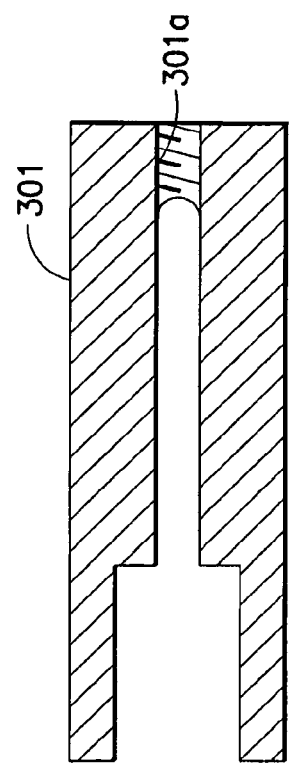
FIG. 28a is a longitudinal sectional view of a self-pushing clip.
Figure 30:
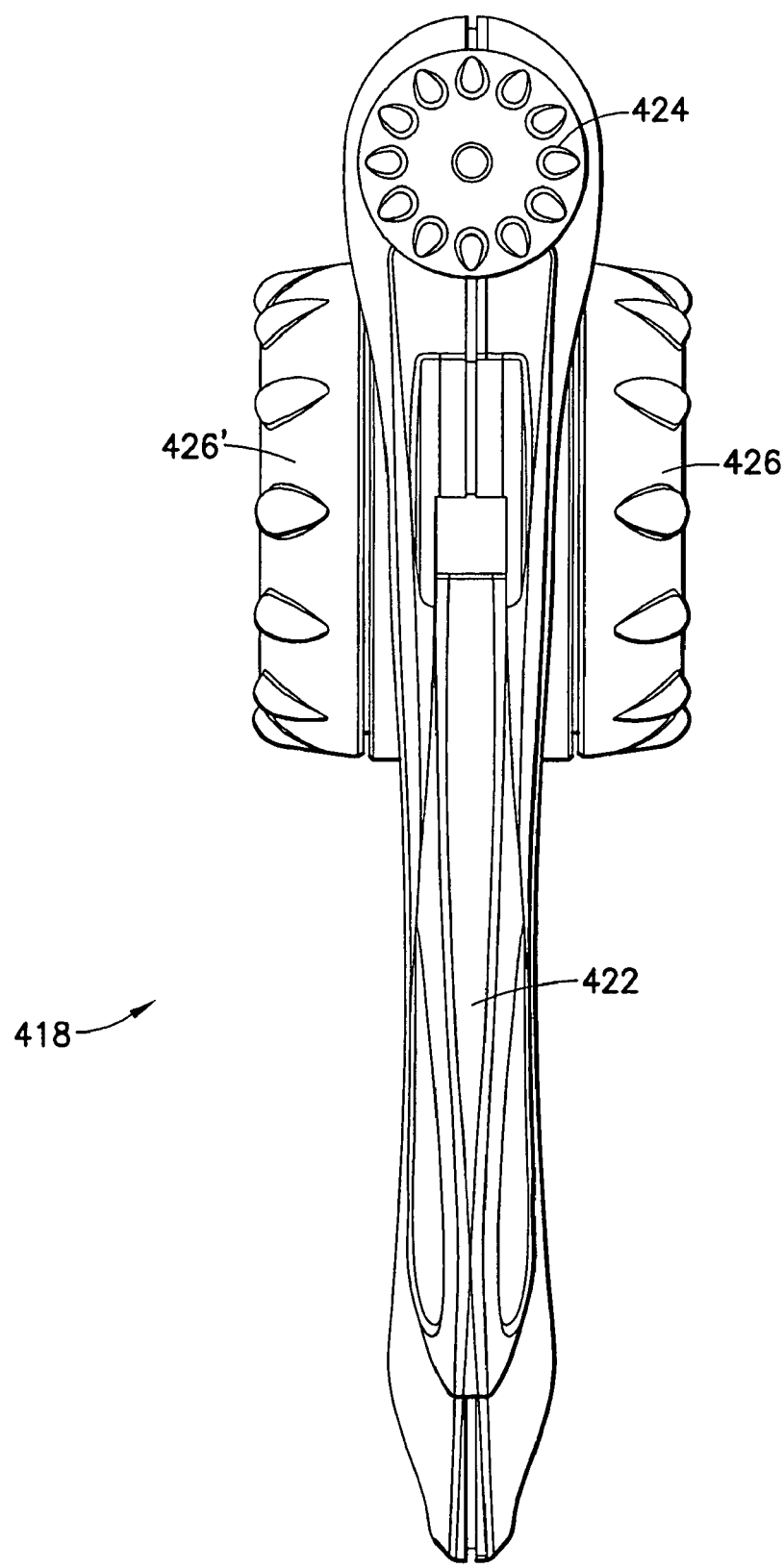
FIG. 30 is a proximal end view of a presently preferred embodiment of the manual actuator.

Referring now to FIGS. 28-30, alternate embodiments of a clip 301 and a clip advancement mechanism are shown. The clip 301 has substantially the same configuration as the clip described above except that it has a threaded hole 301*a* in its proximal end. FIG. 28 shows a plurality of clips 301-304 threadably mounted on the threaded end 148*a* of rotatable control member 148. The control member 148 is similar to the control member 48 described above except that it is mounted in a way that it does not translate relative to the coil or the actuator. In particular, control member 148 is mounted in a thrust collar 310 set in a thrust bearing 312 which is located between the proximal and distal coils (not shown). When the control member 148 is rotated, the clips 301-304 which cannot rotate because of the garage (not shown) are translated through the garage because of their threaded engagement with the control member.

The Presently Preferred Manual Actuator

Figure 31:
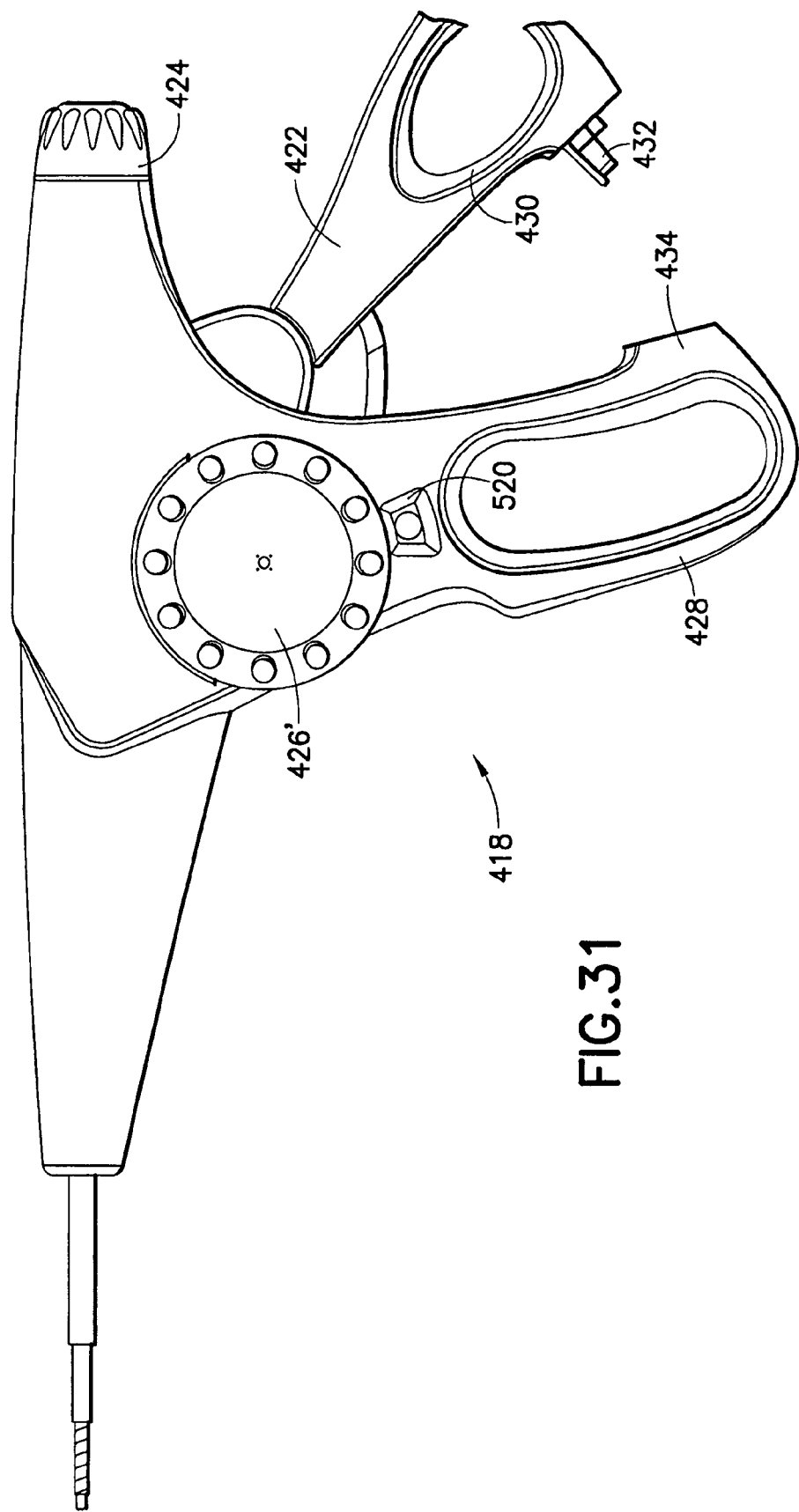
FIG. 31 is a side elevation view of the presently preferred embodiment of the manual actuator.
Figure 32:
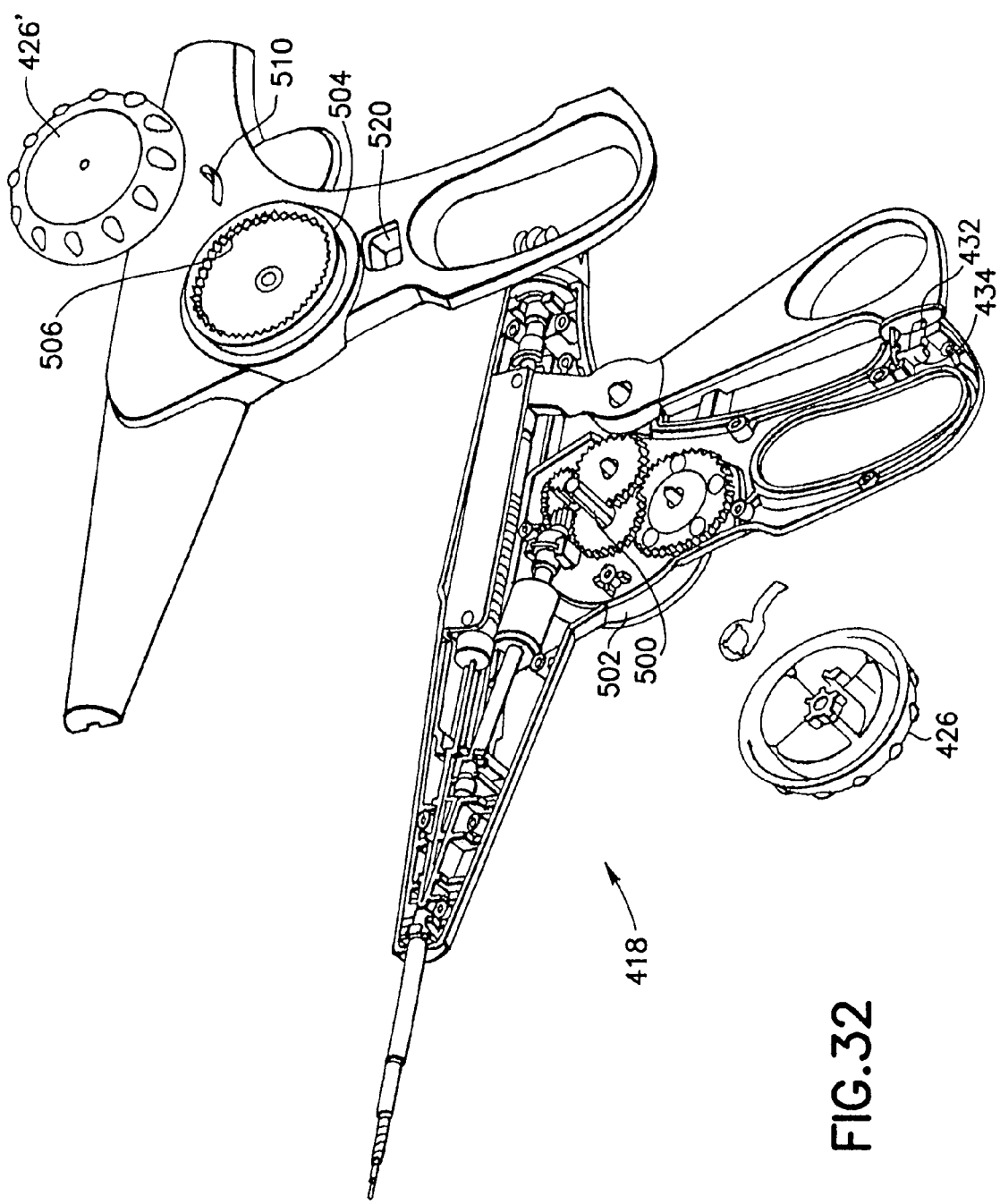
FIG. 32 is an exploded perspective view of the presently preferred embodiment of the manual actuator.
Figure 33:
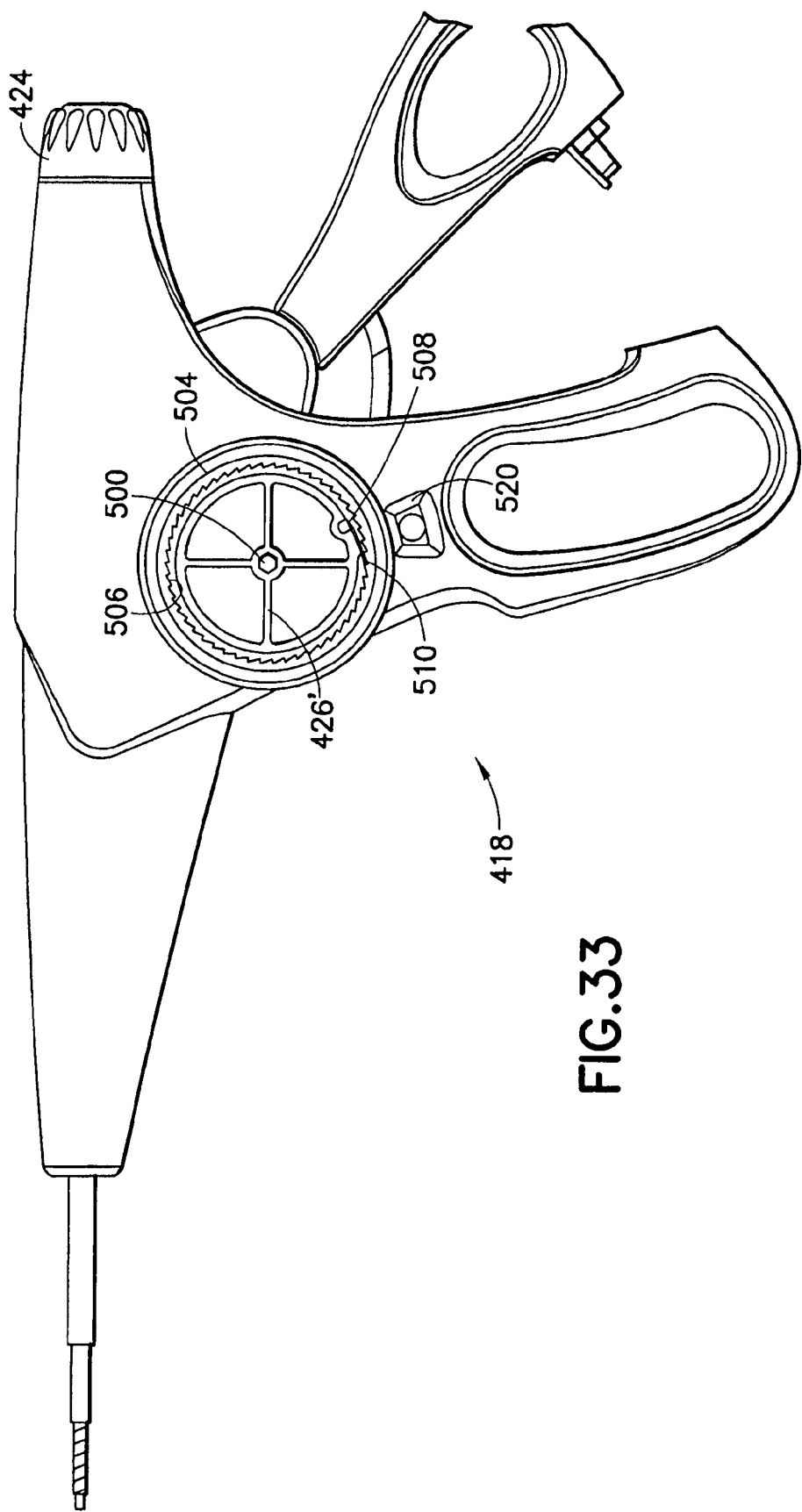
FIG. 33 is a view similar to FIG. 31 with the crank transparent to illustrate the ratchet mechanism.

FIGS. 30-37 illustrate the presently preferred manual actuator 418. Similar reference numerals, increased by 400, refer to similar parts to the manual actuator 18 of FIGS. 1-6. The manual actuator 418 includes a lever 422, a knob 424, and a crank 426. According to a first aspect of this embodiment, a second crank 426' is provided on the opposite side of the actuator. As seen best in FIGS. 30 and 32, the "cranks" 426, 426' are knurled and do not have crank handles like the crank 26. Like the actuator 18, and as seen in FIGS. 31-33, the actuator 418 is provided with a finger grip 428 and a lever 422 having a thumb grip 430. Engaging hooks 432, 434 allow the lever to be releasably locked in the closed position as shown in FIG. 32.

As seen best in FIG. 32, a polygonal crank shaft 500 extends transversely through the actuator 418 and is engaged on opposite ends by the cranks 426, 426'. The crank shaft 500 is surrounded by a cylindrical structure 502, 504 on opposite sides of the actuator 418. According to a second aspect of this embodiment, one of the cylinder structures 504 is provided with a plurality of ratchet teeth 506, and as seen in FIG. 33, the crank 426' has a peripheral post 508 upon which a ratchet pawl 510 is mounted. Those skilled in the art will appreciate that the ratchet and pawl prevent both cranks 426, 426' from being rotated backward, i.e., clockwise in the illustrated embodiment.

Figure 34:
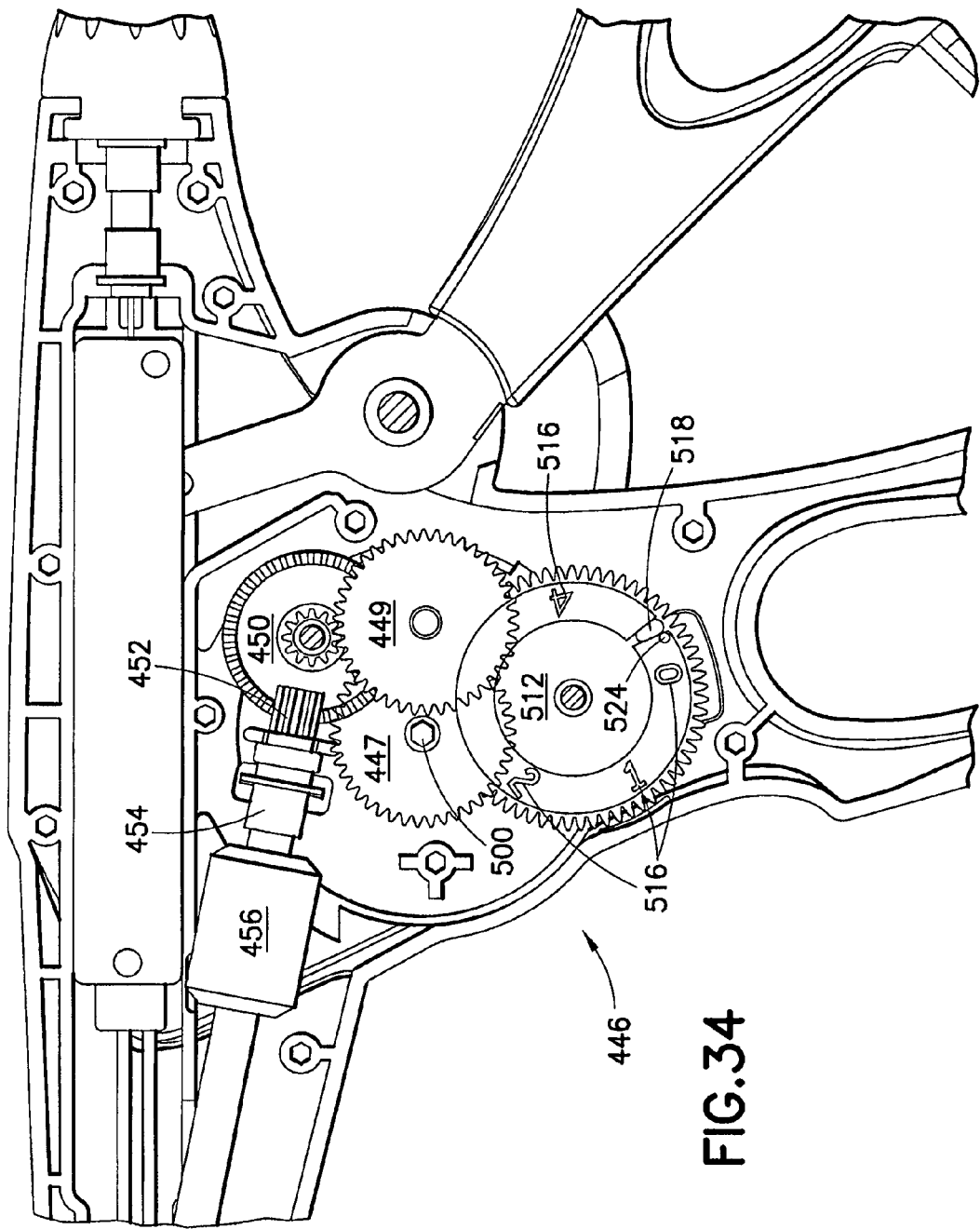
FIG. 34 is an enlarged view of the transmission and counter gears.
Figure 35:
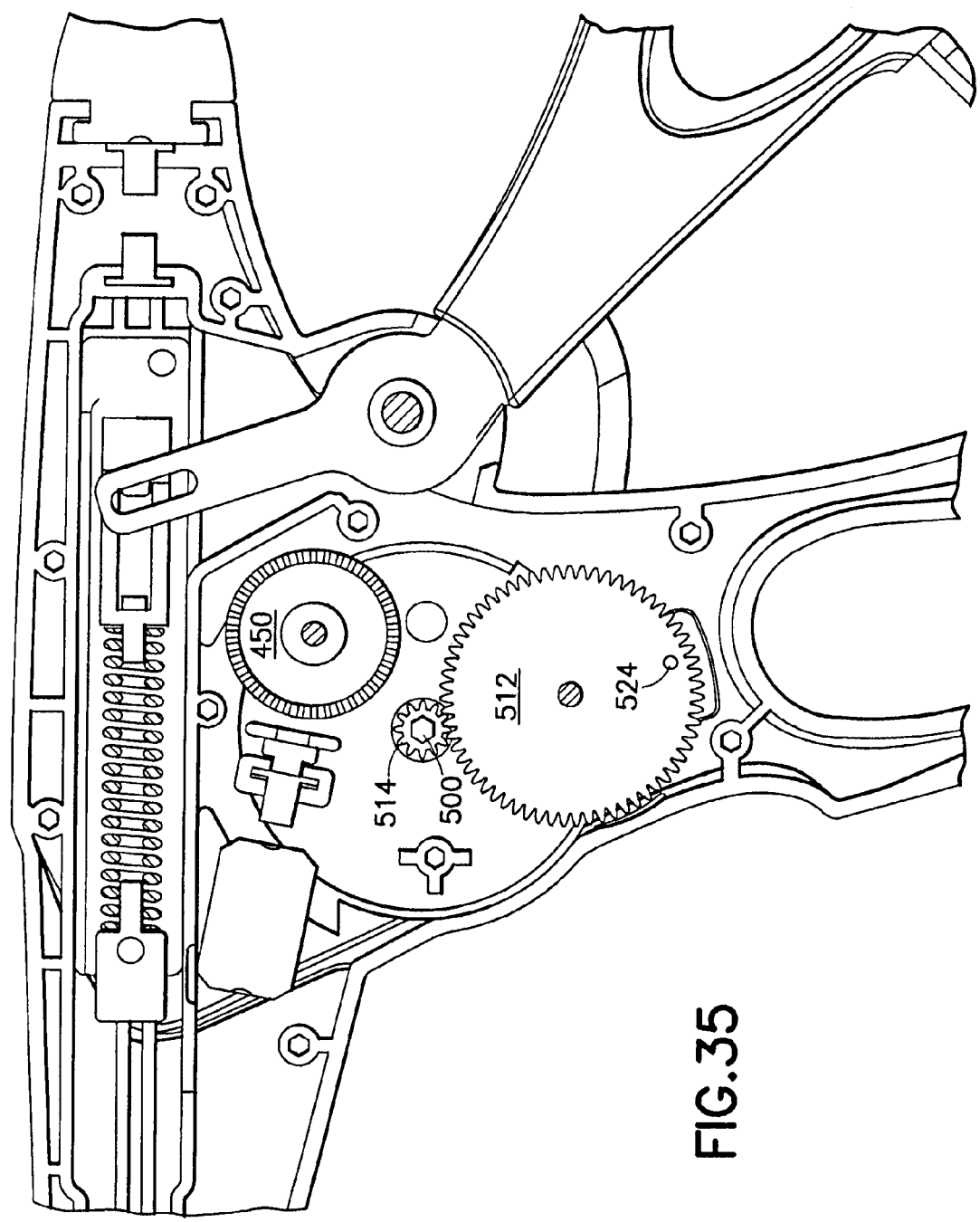
FIG. 35 is a view similar to FIG. 34 with the transmission gears removed showing the connection between the crank shaft and the counter gear.

According to a third aspect of this embodiment, as seen best in FIGS. 34 and 35, the transmission 446 is coupled to a counter gear 512. In this embodiment, the transmission gears are arranged slightly differently than in the embodiment of FIGS. 1-6. In particular, the crank shaft 500 is coupled to a small hub gear 514 which engages the counter gear 512 as shown in FIG. 35. The crank shaft is also coupled to an input spur gear 447 which drives a step up spur gear 449 which is flipped over as compared to the gear 49 shown in FIG. 4. The spur gear 449 drives the crown gear 450 which is coupled to the pinion 452. The pinion 452 is coupled to the cylinder 454 which is turn is coupled to the flywheel 456.

The counter gear 512 is provided with indicia 516, preferably on both sides, and a standing rib 518. The body of the actuator 418 is provided with at least one, but preferably two windows 520, 522 (see FIGS. 31-33, 36 and 37) through which the indicia 516 of the counter gear can be viewed (one at a time). The illustrated counter is for use with a store of five clips. When the garage is full, the portion of the counter between the standing rib 518 and the numeral "4" is visible through the window. In order to accommodate space for the standing rib, the number of teeth on the counter gear is chosen so that one rotation of the hub gear causes slightly less than ⅕ rotation of the counter gear. As clips are dispensed, the counter gear rotates clockwise counting down the number of clips remaining. When there are "0" clips remaining, the "0" indicia is visible through the window. In addition, when in this position, the standing rib 518 abuts a structure inside the actuator, e.g. a wall of the window opening. This prevents the counter gear and the cranks from advancing further. Preferably, the counter gear 512 is provided with an index hole 524 which is used to properly orient the gear during assembly.

Those skilled in the art will appreciate that means other than the standing rib 518 could be used to stop rotation. For example, the threads on the control member 48 can be arranged to run out upon dispensing the last clip. Alternatively, a bump can be provided on the control member 48 at a location to be stopped by engaging the rigid member 60 upon dispensing the last clip. Still another alternative is to arrange the pusher 70 to engage and lock on the detent fingers 80*m*, 80*n* after the last clip has been fired. The purpose of the stop is to prevent the pusher from entering the jaws and to indicate that all of the clips have been used.

Figure 36:
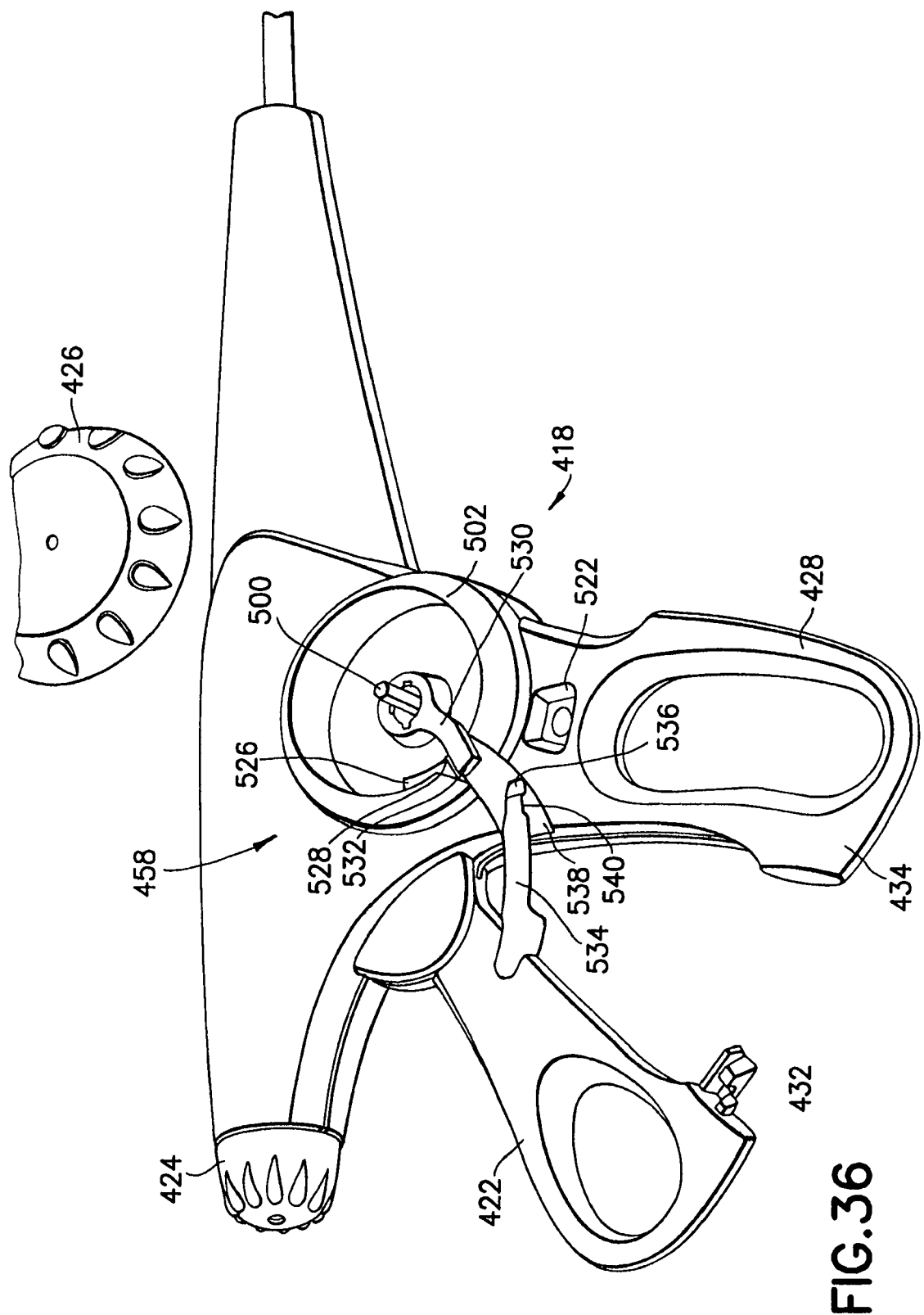
FIG. 36 is an exploded perspective view of the presently preferred embodiment of the manual actuator showing the detent lock engagable by the lever.
Figure 37:
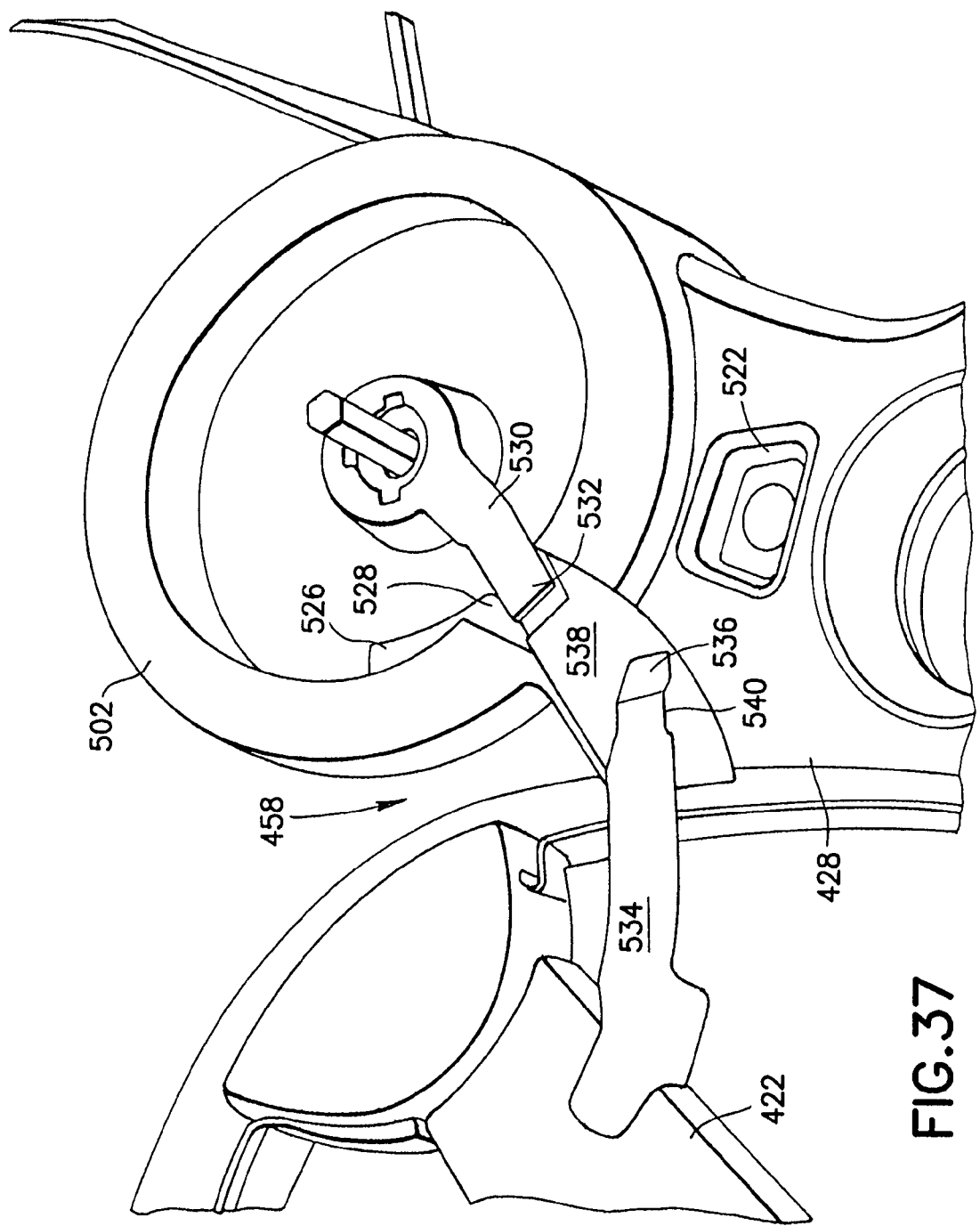
FIG. 37 is an enlarged view of the lock mechanism of FIG. 36.

According to a fourth aspect of this embodiment and as illustrated in FIGS. 36 and 37, the crank detent lock 458 is engaged by the lever 422 such that the crank can only be turned when the jaws are closed. In particular, the floor of the previously identified cylindrical structure 502 is provided with a ramp 526 which rises to a step 528. The crank 426 and/or the crank shaft 500 are/is coupled to a leaf spring 530 which extends generally radially out from the axis of the crank shaft and terminates with an upturned lip 532. FIGS. 36 and 37 illustrate the crank/crank shaft in the locked position with the leaf spring 530 lying adjacent the step 528. If the crank were operated to dispense a clip, rotation of the crank would be stopped by the leaf spring 530 hitting the step 528.

The lever 422 has a tongue 534 with a lifting ramp 536 at its end. A mouth 538 opens into the cylindrical structure 502 adjacent to the step 528. The tongue 534 is arranged so that it enters the mouth 538 when the lever 422 is moved to the closed position, closing the jaws. When the tongue 534 enters the mouth 538, the lifting ramp 536 engages the upturned lip 532 and raises the leaf spring 530 above the step 528. In this position, the leaf spring and the step no longer impede rotation of the cranks, and a clip may be dispensed. Rotation of the crank moves the leaf spring down the ramp 526 onto the floor of the cylindrical structure where it is free to move around in a complete rotation. The tongue 534 is provided with a lower recess 540 which allows the leaf spring 530 to pass under it at the end of a single rotation of the crank, at which point the spring will once again abut the step 528. The tongue 534 is resilient enough so that the recess 540 can pass over the upturned lip 532 when the lever 422 is moved back to open the jaws. Thus, the crank will move exactly one rotation after the jaws are closed and will not move again until the jaws are opened and then closed again.

Alternate Embodiments of Force Limiting Springs

Figure 38:
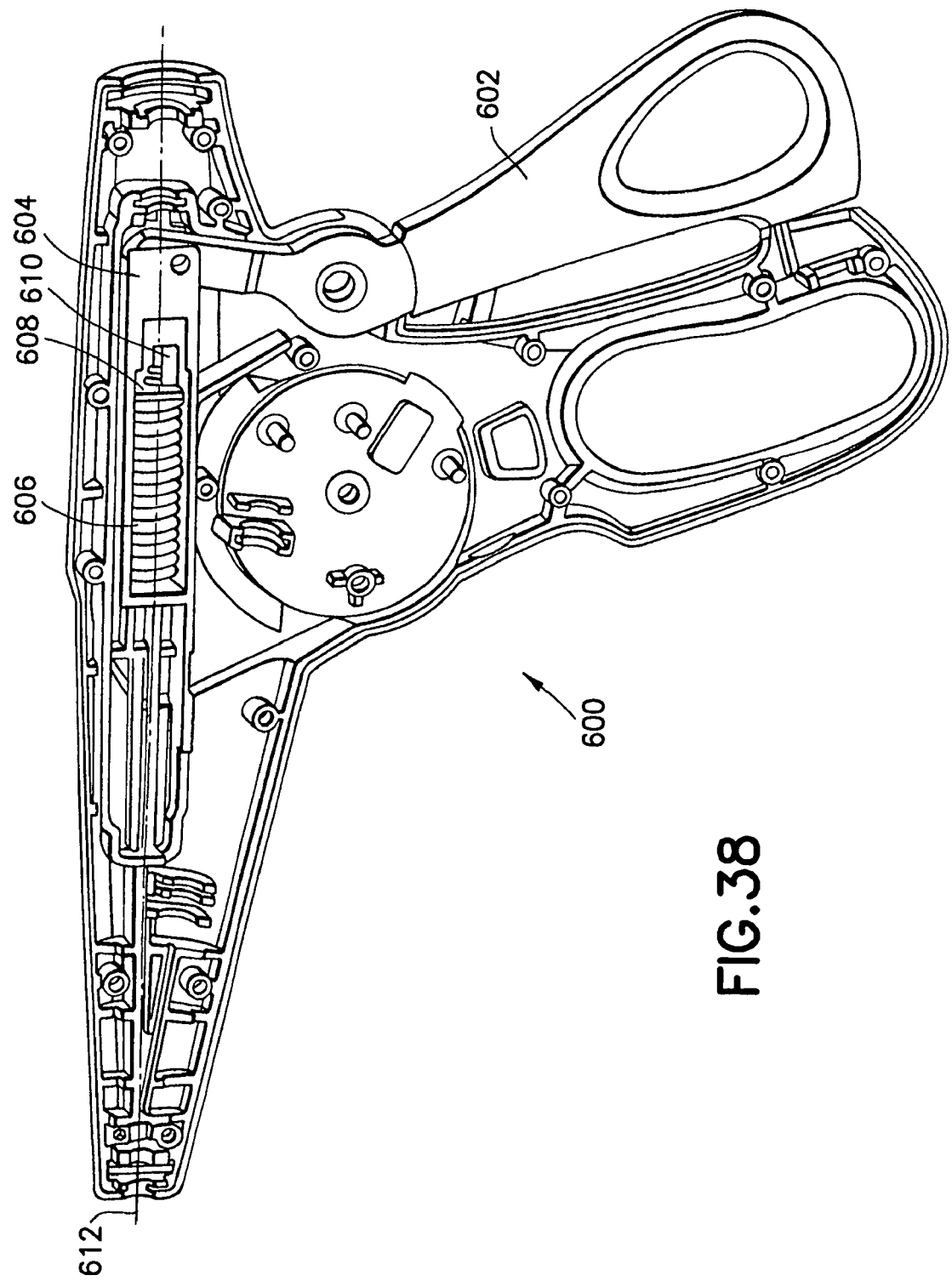
FIG. 38 is a partially disassembled perspective view of a manual actuator having an alternate embodiment of a force limiting spring assembly using a shuttle element.
Figure 39:
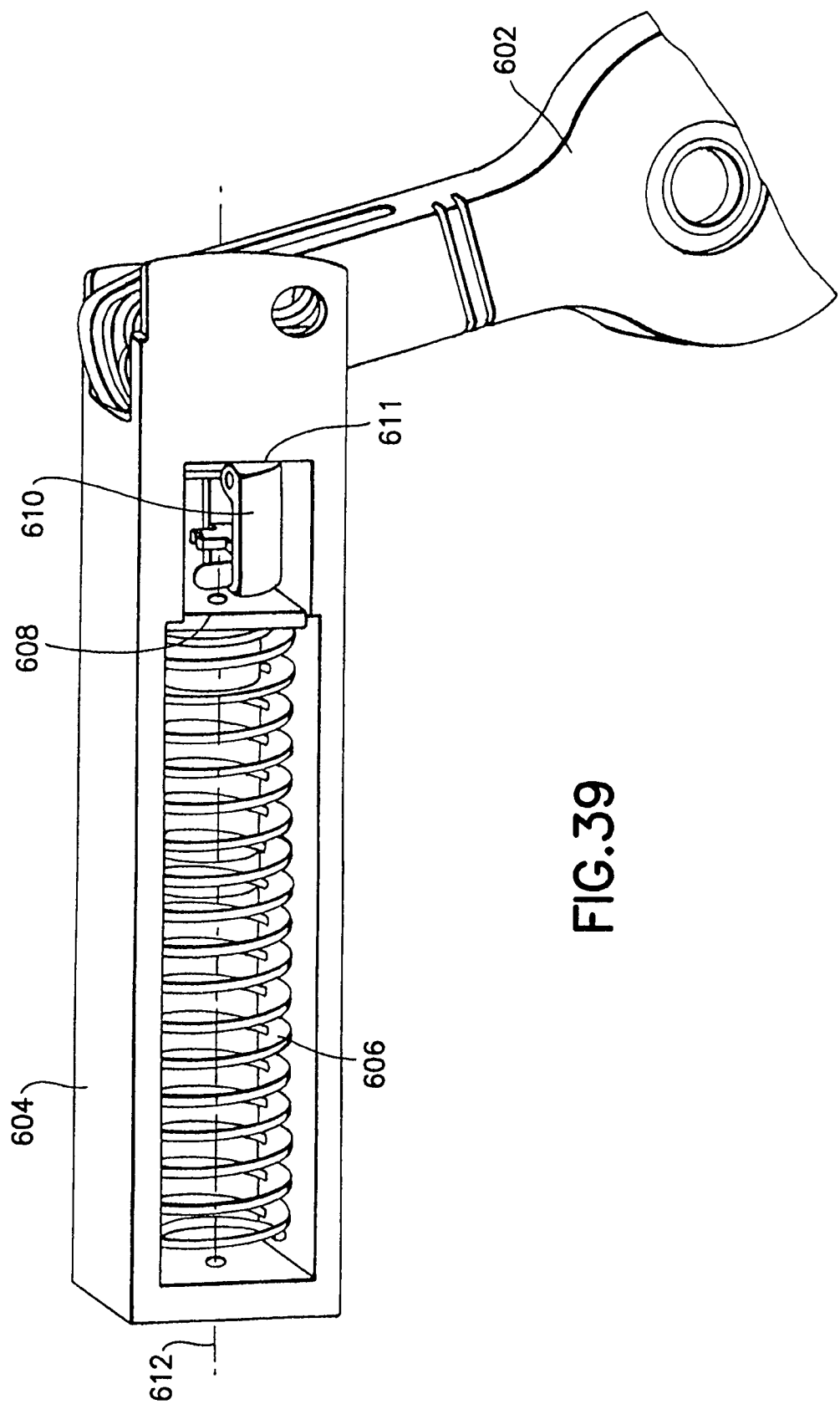
FIG. 39 is a broken enlarged view of the spring assembly of FIG. 38.
Figure 40:
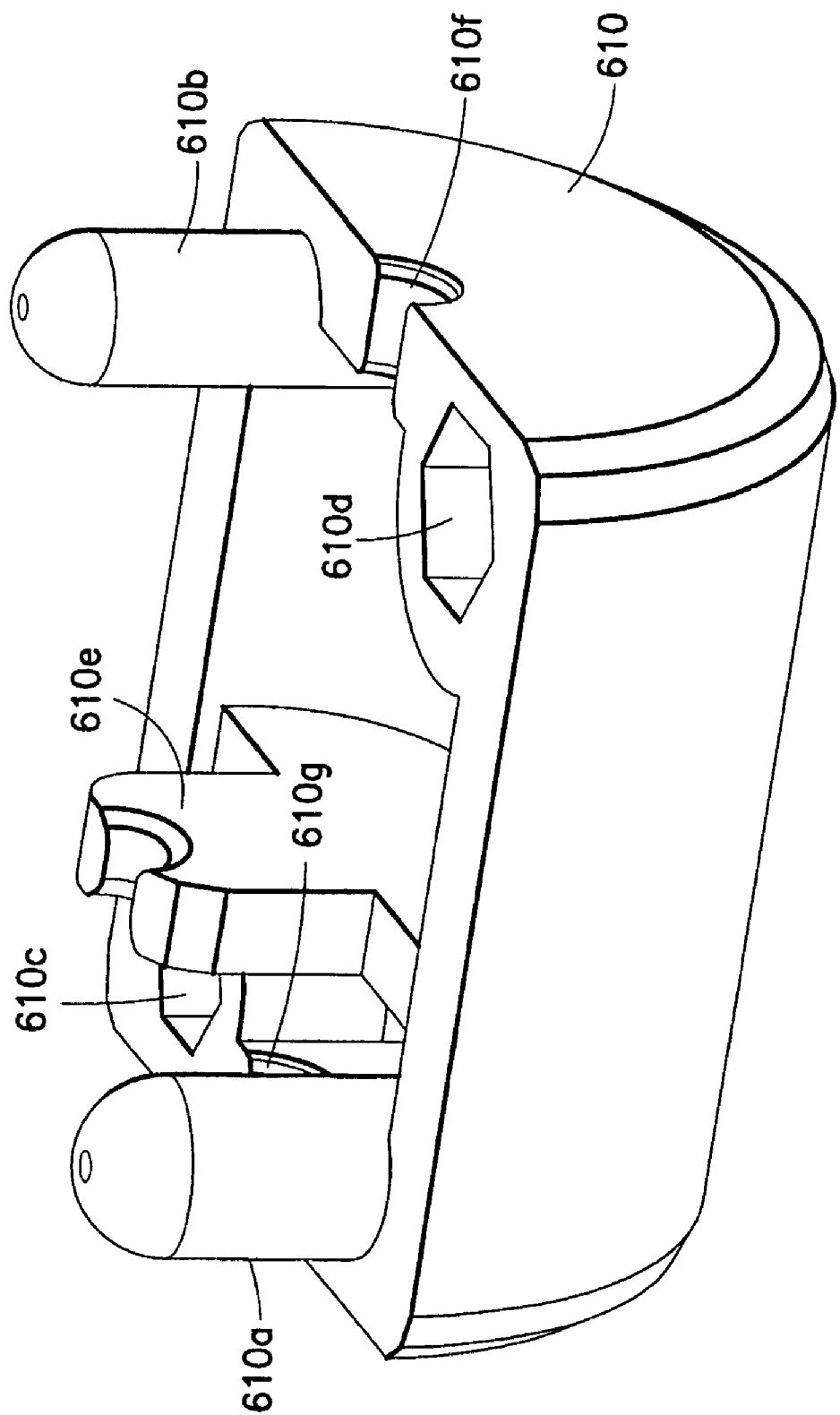
FIG. 40 is an enlarged perspective view of an hermaphroditic part used to form the shuttle element.

FIGS. 38-40 illustrate a first alternate embodiment of a force limiting spring in a manual actuator 600 which in other respects is substantially the same as the actuator described above. The actuator 600 has a thumb lever 602 which is coupled to a linkage 604. The distal end of the linkage 604 engages the distal end of a spring 606. A washer 608 is located adjacent the proximal end of the spring 606 and a "shuttle" 610 is located proximal of the washer 608 and abuts a stop wall 611 on the linkage 604. The control member 612 extends through the linkage 604, the spring 606, the washer 608, and is coupled to the shuttle 610. The shuttle 610 is composed of two identical pieces illustrated in FIG. 40. Each piece 610 is generally semi-cylindrical, has a pair of locking nubs 610a, 610b and a pair of nub-receiving sockets 610c, 610d. The interior of the piece 610 has an off center wire engaging tongue 610e and each end is provided with an axial half bore 610f, 610g. From the foregoing, those skilled in the art will appreciate that when a control wire is placed between the two pieces of the shuttle and they are pressed together, the control wire will be bent into an S shape by the two tongues 610e and the shuttle will be fixed relative to the control wire.

With the foregoing in mind, it will also be appreciated that when the lever 602 is moved from the open position (FIG. 39) toward the closed position shown in FIG. 38, the linkage 604 moves the spring 606 and washer 608 proximally against the shuttle 610 pulling the control wire 612 proximally until the control wire can be pulled no more, or until a predetermined tension is placed on the wire. At that point, further closure of lever 602 continues to move the linkage 604 and spring 606 proximally. However, because the wire 612, washer 608, and shuttle 610 will not move (or because the spring constant is less than the tension on the wire), the spring 606 begins to compress between the linkage 604 and the washer 608 and remains compressed when the lever is locked. The amount of compression will depend on the tortuosity of the path of the control wire. According to the presently preferred embodiment, there is always some spring compression when the lever is locked as shown in FIG. 38. When the lever 602 is released, at first, the linkage 604 will move distally relative to the washer and shuttle and the spring will expand. Eventually, the stop wall 611 on the linkage 604 will reach the shuttle 610 and push the shuttle distally, thereby causing the control wire 612 to move distally.

It will be appreciated by those skilled in the art that the function of the washer 608 is to provide a positive interference between the spring 606 and the shuttle 610. One manner of providing the positive interference is to partially close the end of spring 606 by bending the end of the spring 606 into an "e" shape. Alternatively, the end of the spring wire can be flattened and broadened to interfere with the shuttle. It will also be appreciated by those skilled in the art that instead of providing a stop wall 611 on the linkage 604 for the shuttle 610, the lever 602 can be arranged to directly push the shuttle (and hence wire 612) distally upon the release of the lever from the closed position.

Figure 41:
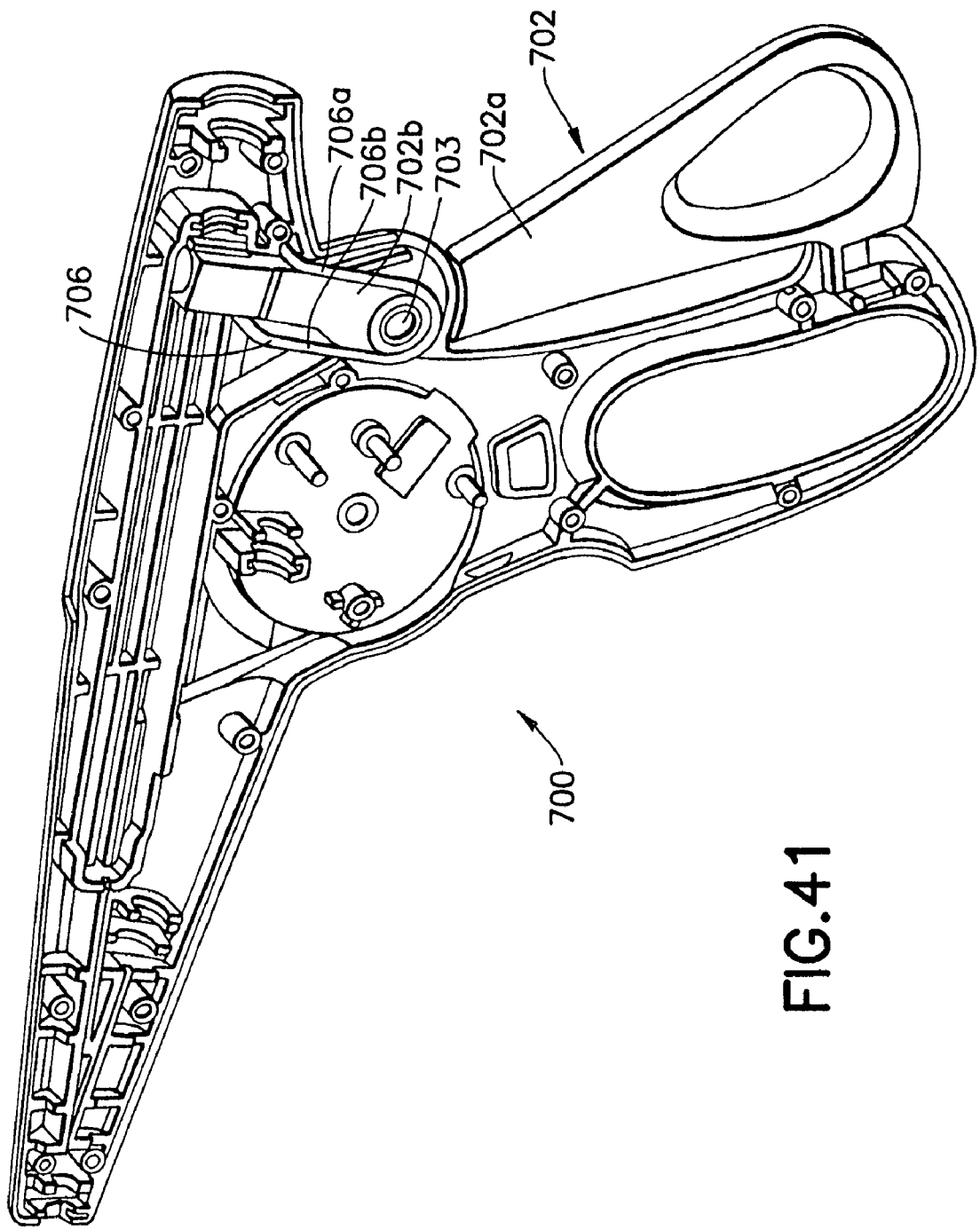
FIG. 41 is a view similar to FIG. 38 showing an alternate embodiment of a force limiting device in the form of a spring-hinged lever.
Figure 42:
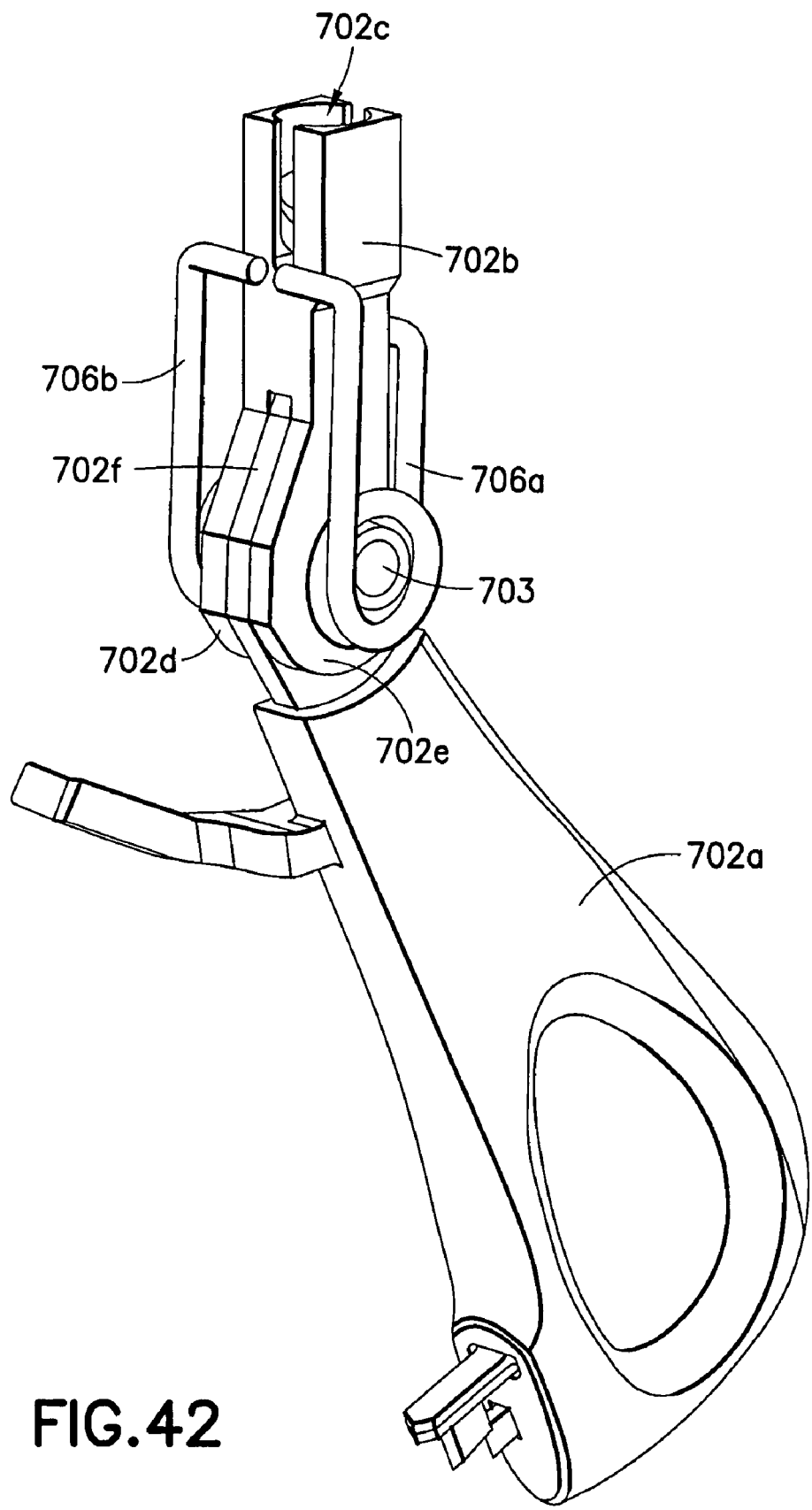
FIG. 42 is a perspective view of the spring-hinged lever.
Figure 43:
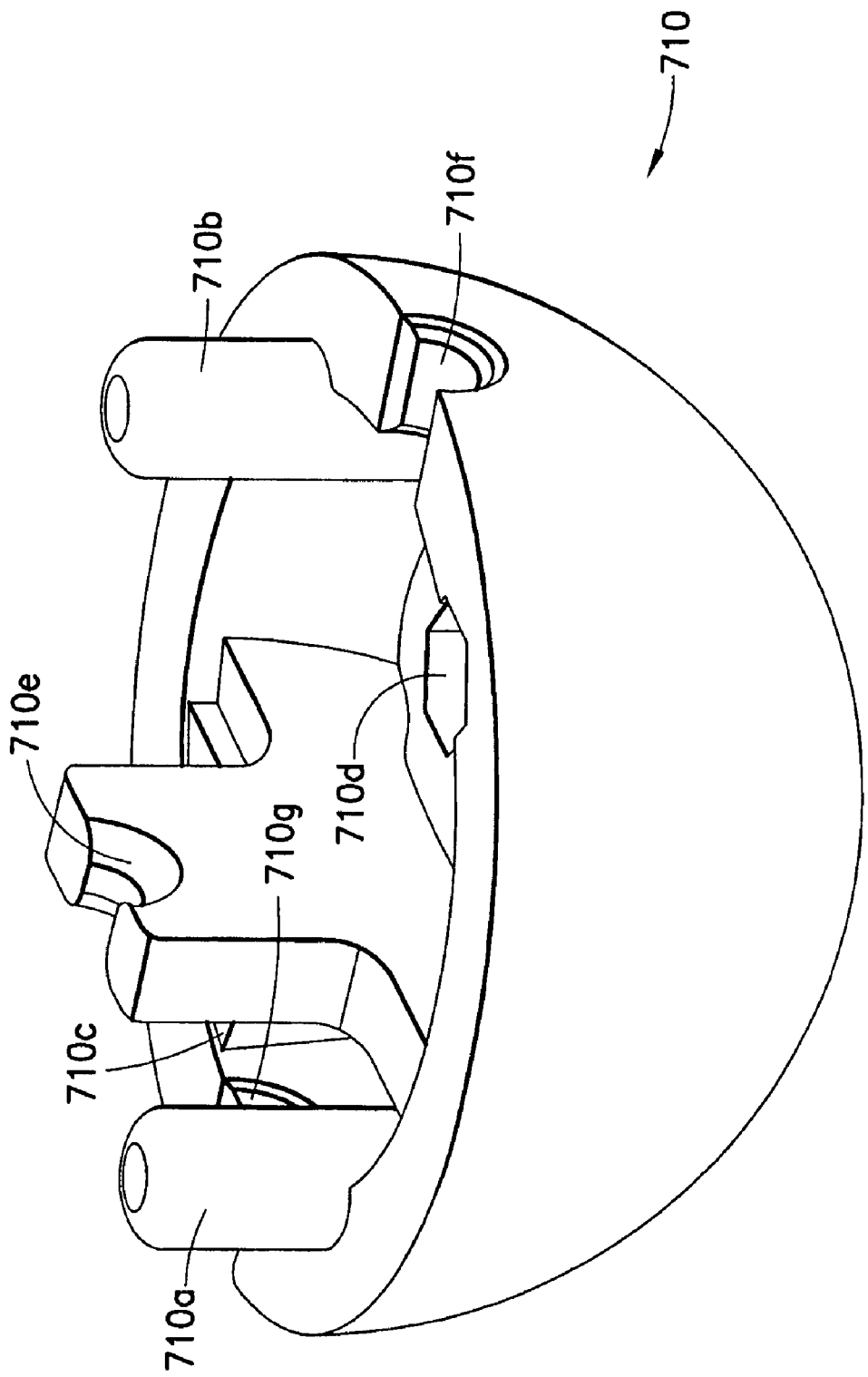
FIG. 43 is an enlarged perspective view of an hermaphroditic part used to form a ball joint coupling between the control member and the spring-hinged lever.

FIGS. 41-43 illustrate a second alternate embodiment of a force limiting spring in a manual actuator 700 which in other respects is substantially the same as the actuator described above. The actuator 700 has a thumb lever 702 which is formed in two parts 702a, 702b coupled to each other by a torsion spring 706. As seen best in FIG. 42, the upper part 702b of the lever 702 has a socket 702c for receiving a ball 710 coupled to the control wire (not shown) and two spaced apart legs 702d, 702e. The lower part 702a of the lever has an upper finger 702f which extends between the legs 702d, 702e. The torsion spring 706 is mounted on a pivot axle 703 which extends through the upper finger 702f and the legs 702d, 702e. The back of the spring 706a engages the back of the finger 702f and the front of the spring 706b engages the upper part of the lever 702b. The ball is made of two identical pieces illustrated in FIG. 43. The piece is generally hemispherical but is similar to the previously described shuttle in that it has a pair of locking nubs 710a, 710b and a pair of nub-receiving sockets 710c, 710d. The interior of the piece 710 has an off center wire engaging tongue 710e and a pair of diametrically opposed half bores 710f, 710g are provided coaxial with the tongue 710e. From the foregoing, those skilled in the art will appreciate that when a control wire is placed between the two pieces of the ball and they are pressed together, the control wire will be bent into an S shape by the two tongues 710e and the ball will be fixed relative to the control wire.

With the foregoing in mind, it will be appreciated that when the lever 702 is moved from an open position toward the closed position shown in FIG. 41, the upper part 702b of the lever and the control wire (not shown) are moved proximally until the control wire cannot be pulled further. At this point, the upper part 702b of the lever remains stationary. However, in order to reach a fully closed lever position, the lower lever part 702a can continue to rotate about the pivot axle 703 and cause the finger 702f to exert force against the back part 706a of the spring 706, thereby causing the spring front part 706b to spread away from spring back part 706a and top lever part 702b. When the lever is eventually released from its fully closed position, at first the force of finger 702f against the spring is released and the ball 710 and wire will not move. Eventually, when spring front part 706b hits the top lever part 702b, the entire lever, the ball 710 and the control wire are moved distally.

Pre-loaded Clip Ejector

In the presently preferred embodiment, at least a distal portion of the flexible coil (in this case the distal coil 12b) is pre-loaded to provide sufficient columnar stiffness. When the jaws 84, 86 are closed, the pull wire(s) increase the load between the clevis and the nut. After the clip is deployed, the pull wires are actuated distally to open the jaws. The force of the compressed clip train, and if necessary, the force from the pull wires is sufficient to overcome the pre-load of the distal coil so that the jaws and clevis move away from the tines of the clip, which have been compressed against the forming anvils of the jaws. An alternate embodiment of this concept provides oblong holes in the jaws for attachment to the bosses on the clevis. When the jaws are closed, the pull wires move the jaws proximally with respect to the clevis. When the pull wires are released from tension and actuated distally, the jaws are also able to move distally with respect to the clevis to release the compressive load on the tines of the clip.

According to an alternative embodiment, the distal coil 12b is pre-loaded to spring distally. When the jaws 84, 86 are closed, the pull wire(s) 62 pull against the distal coil, shortening the distal coil against its pre-load. After the clip is dispensed, the jaws are opened. When the jaws are opened, the pre-load on the distal coil causes the clevis 82, jaws 84, 86, and garage 80 all to move a slight distance distally. At the same time, the clips do not move, as they are freely disposed in the garage which is moving over them. This action has the effect of separating the distal anvils on the jaws from the tines on the formed clip, thereby easing the opening of the jaws.

The pre-loading of the distal coil provides the coil with sufficient columnar strength to allow for tangential bites, prevents buckling during jaw closure, and provides reaction force to overcome frictional forces as the jaws open.

Alternate Jaw Embodiment

Figure 44:
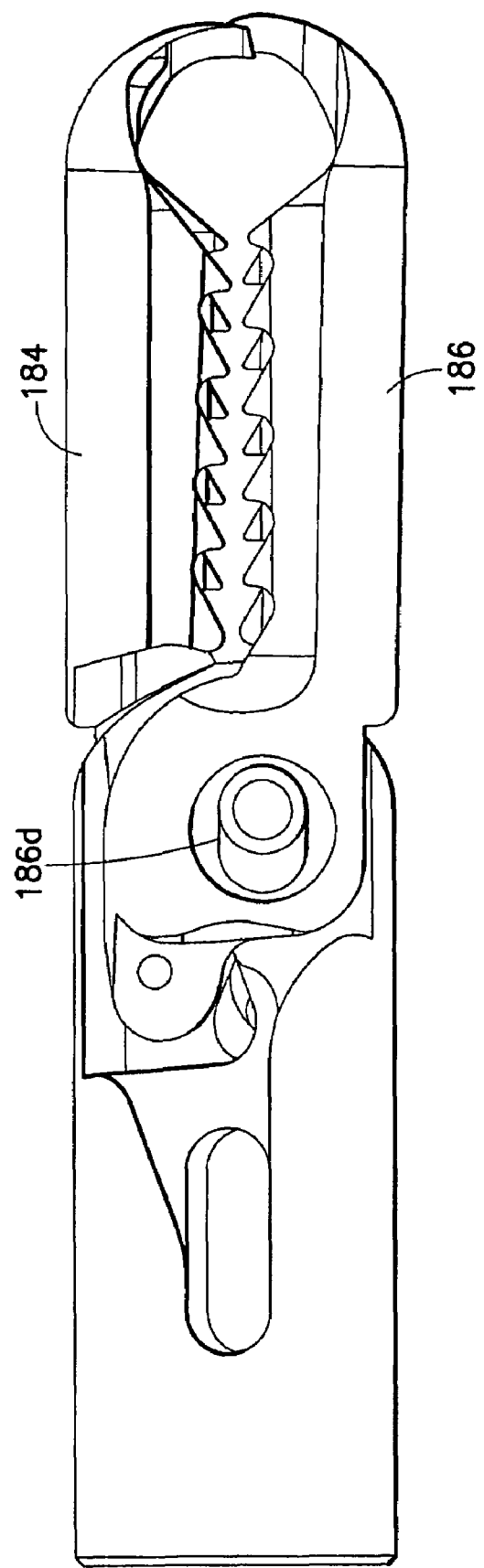
FIG. 44 is a view similar to FIG. 20 but of an alternate jaw embodiment.
Figure 45:
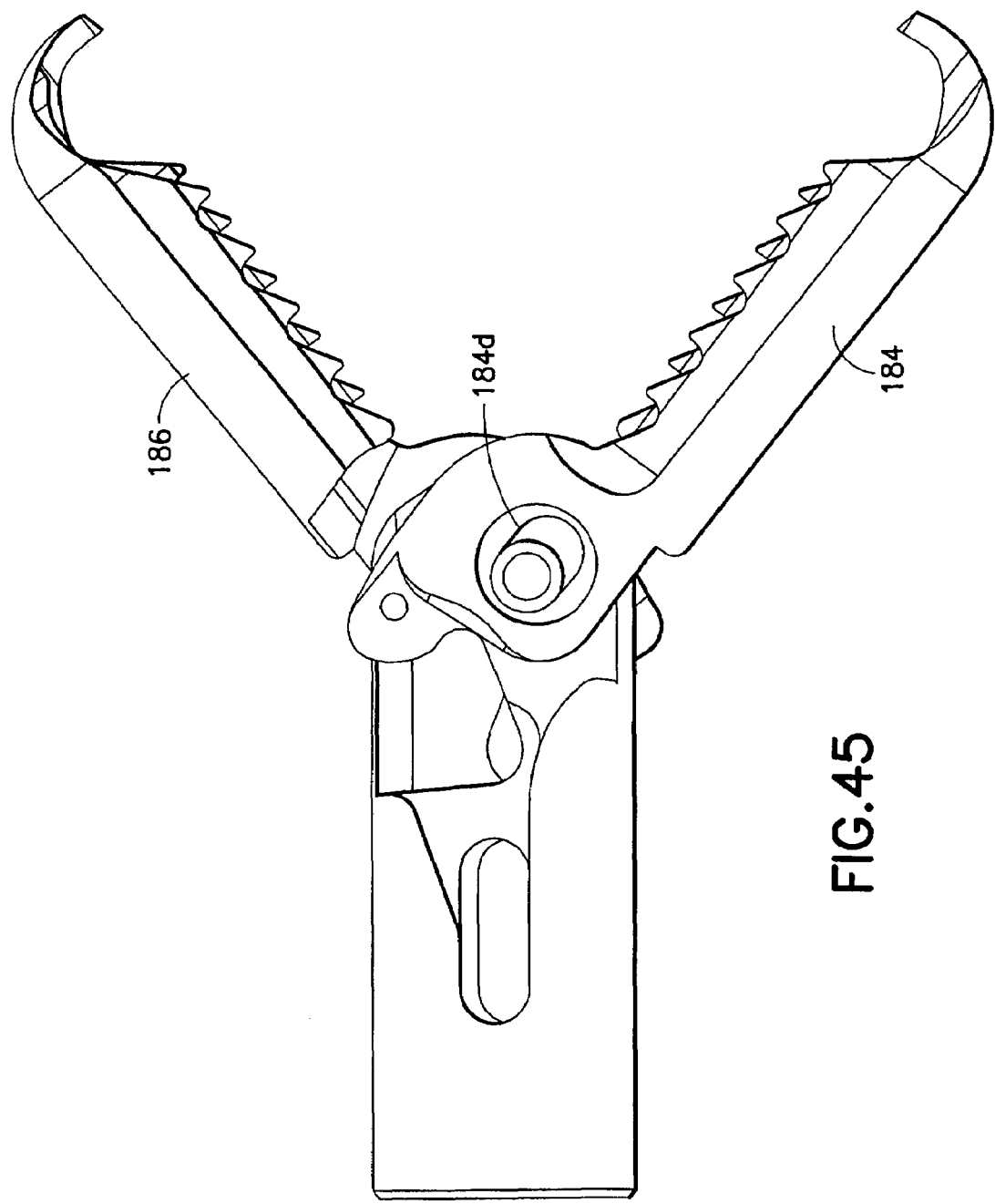
FIG. 45 is a view similar to FIG. 18 but of the alternate jaw embodiment of FIG. 44.

FIGS. 44 and 45 illustrate an alternate embodiment of jaws 184, 186 which are substantially the same as the jaws 84, 86 but for their mounting holes 184d, 186d. In this embodiment, the mounting holes 184d, 186d are not circular. They are oblate or "slotted". This allows the jaws to slide distally and proximally as they are opened and closed. Thus, when the jaws are closed as shown in FIG. 44, they are pulled proximally. In this position, the clip is fired into the closed jaws which act as forming anvils as described above. When the jaws are opened as shown in FIG. 45, they slide distally away from the formed clip separating the distal anvils on the jaws from the tines on the formed clip, thereby easing the opening of the jaws.

There have been described and illustrated herein several embodiments of a flexible endoscopic clip applier. While particular embodiments of the invention have been described, it is not intended that the invention be limited thereto, as it is intended that the invention be as broad in scope as the art will allow and that the specification be read likewise. Thus, while the coils of the invention have been described as being formed from flat stock, it will be appreciated that the stock can be of circular or other cross-section. Also, while particular materials have been described as preferred in making various of the elements of the invention, it will be appreciated that other materials can be utilized. Further, while the invention has been described as utilizing a gear arrangement which provides a specific number of turns to a wire control element for advancing the clips, it will be appreciated that other gear arrangements which provide the same or different numbers of turns of the wire control element can be provided. Further, while the invention has been disclosed in conjunction with two different kinds of end effectors, i.e. the jaws and the clip pusher, other components of the invention may be used with different end effectors. It will therefore be appreciated by those skilled in the art that yet other modifications could be made to the provided invention without deviating from its spirit and scope as claimed.

What is claimed is:

1. An endoscopic surgical instrument, comprising:
   a flexible tube having a proximal end and a distal end;
   a threaded member coupled to said flexible tube toward said distal end of said flexible tube;
   an end effector coupled to or housed within said distal end of said flexible tube;
   an actuator coupled to said proximal end of said flexible tube;
   a threaded control member extending through said flexible tube and engaging said threaded member, said threaded control member coupled to said end effector and to said actuator, wherein
   said actuator rotates said threaded control member and thereby translates said threaded control member relative to said threaded member to operate said end effector,
   said flexible tube comprises a first flexible tube having a proximal end and a distal end, and a second flexible tube having a proximal end and a distal end,
   said threaded member being coupled between said distal end of said first flexible tube and proximal end of said second flexible tube,
   said end effector coupled to or housed within said distal end of said second flexible tube, and
   said actuator coupled to said proximal end of said first flexible tube.

2. The instrument according to claim 1, further comprising:
   a torque providing member coupled to said actuator and extending through said first flexible tube,
   said threaded member having an off axis bore which receives said torque providing member, whereby
   rotation of said torque providing member causes rotation of said threaded member and said second flexible tube.

3. An endoscopic surgical instrument, comprising:
   a flexible tube having a proximal end and a distal end;
   a connecting member coupled to said flexible tube toward said distal end of said flexible tube, said connecting member having an axially offset bore;
   an end effector coupled to or housed within said distal end of said flexible tube;
   an actuator coupled to said proximal end of said flexible tube;
   a torque providing control member coupled to said actuator and extending through said flexible tube into said axially offset bore;
   at least one control wire coupled to said end effector and said torque providing control member, wherein
   rotation of said torque providing control member causes rotation of said end effector about a first axis and translation of said torque providing control member causes rotation of said end effector about a second axis,
   said flexible tube comprises a first flexible tube having a proximal end and a distal end, and a second flexible tube having a proximal end and a distal end,
   said connecting member being coupled between said distal end of said first flexible tube and proximal end of said second flexible tube,
   said end effector coupled to or housed within said distal end of said second flexible tube, and
   said actuator coupled to said proximal end of said first flexible tube.

* * * * *